United States Patent
Okazaki et al.

(10) Patent No.: US 9,408,667 B2
(45) Date of Patent: Aug. 9, 2016

(54) GUIDE SHEATH AND GUIDE SHEATH SYSTEM

(71) Applicant: OLYMPUS CORPORATION, Tokyo (JP)

(72) Inventors: Yoshiro Okazaki, Tokyo (JP); Hiromu Ikeda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/057,150

(22) Filed: Oct. 18, 2013

(65) Prior Publication Data

US 2014/0046343 A1 Feb. 13, 2014

Related U.S. Application Data

(63) Continuation of application No. PCT/JP2012/060593, filed on Apr. 19, 2012.

(30) Foreign Application Priority Data

Apr. 26, 2011 (JP) ................................. 2011-098631

(51) Int. Cl.
*A61M 29/00* (2006.01)
*A61B 19/00* (2006.01)
*A61B 1/00* (2006.01)
*A61M 25/06* (2006.01)
*A61B 17/00* (2006.01)
(Continued)

(52) U.S. Cl.
CPC ............ *A61B 19/201* (2013.01); *A61B 1/00154* (2013.01); *A61B 17/00234* (2013.01); *A61M 5/007* (2013.01); *A61M 25/0662* (2013.01); *A61M 25/09* (2013.01); *A61M 25/007* (2013.01);
(Continued)

(58) Field of Classification Search
CPC .......... A61B 17/00234; A61B 19/201; A61B 1/00154; A61M 2025/09133; A61M 25/0041
USPC ......... 600/101–104, 115, 121, 124, 129, 139, 600/145, 149; 606/191, 193, 194, 198
See application file for complete search history.

(56) References Cited

U.S. PATENT DOCUMENTS 3,160,158 A * 12/1964 Rayhart ........................ 604/179
5,122,122 A *  6/1992 Allgood ........................ 604/174
(Continued)

FOREIGN PATENT DOCUMENTS

CN     101505823 A     8/2009
DE       9409863 U1 *  3/1995
(Continued)

OTHER PUBLICATIONS

International Search Report dated Jul. 10, 2012 issued in PCT/JP2012/060593.

*Primary Examiner* — Ashley Fishback
(74) *Attorney, Agent, or Firm* — Scully, Scott, Murphy & Presser, PC

(57) ABSTRACT

Provided is a guide sheath that is prevented from coming out of a body cavity so as to allow for stable operation. A tubular guide sheath that guides an insertion section of a medical device to be inserted into a body cavity includes a base-end opening that is provided at a base end of the guide sheath and into which the insertion section is inserted; a distal-end opening that is provided at a distal end of the guide sheath; a flexible bent section that is provided at the distal end of the guide sheath and is elastically bent; and an exit opening that is provided in an outer side surface of the bent section and from which the insertion section extends out.

12 Claims, 23 Drawing Sheets

(51) Int. Cl.

| | | |
|---|---|---|
| *A61M 5/00* | (2006.01) | |
| *A61M 25/09* | (2006.01) | |
| *G02B 23/24* | (2006.01) | |
| *A61M 25/00* | (2006.01) | |
| *A61M 25/01* | (2006.01) | |

(52) U.S. Cl.
CPC ........ *A61M 25/0041* (2013.01); *A61M 25/0102* (2013.01); *A61M 25/0108* (2013.01); *A61M 25/0147* (2013.01); *A61M 29/00* (2013.01); *A61M 2025/09133* (2013.01); *G02B 23/2476* (2013.01)

(56) References Cited

U.S. PATENT DOCUMENTS

| | | | |
|---|---|---|---|
| 5,630,823 A | 5/1997 | Schmitz-Rode et al. | |
| 7,920,921 B2 * | 4/2011 | Syed et al. | 607/40 |
| 2005/0256452 A1 * | 11/2005 | DeMarchi et al. | 604/95.04 |
| 2008/0051629 A1 | 2/2008 | Sugiyama et al. | |
| 2009/0187207 A1 * | 7/2009 | Saito | 606/192 |

FOREIGN PATENT DOCUMENTS

| | | |
|---|---|---|
| JP | 05-137792 A | 6/1993 |
| JP | 08-043745 A | 2/1996 |
| JP | H09-28666 A | 2/1997 |
| JP | 2000-37347 A | 2/2000 |
| JP | 2003-102843 A | 4/2003 |
| JP | 2005-204728 A | 8/2005 |
| JP | 2005-536262 A | 12/2005 |
| JP | 2008-048946 A | 3/2008 |
| JP | 2011-67597 A | 4/2011 |
| WO | 2004/018029 A2 | 3/2004 |

* cited by examiner

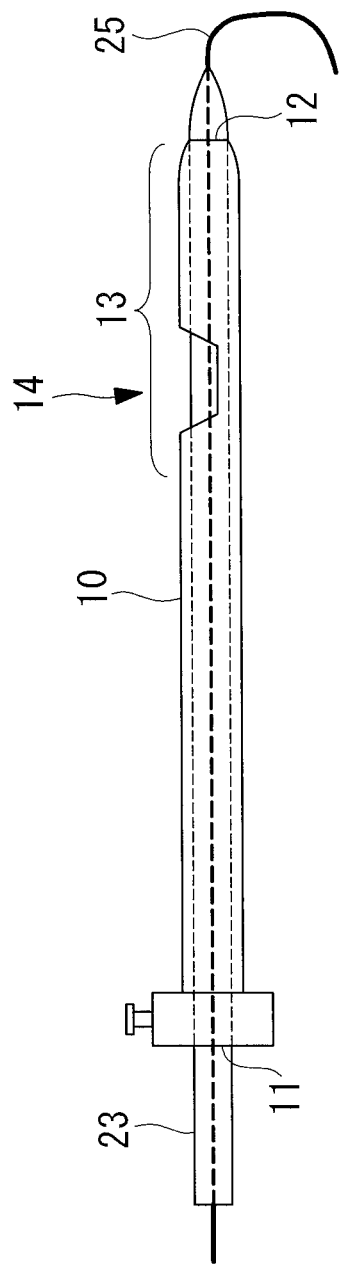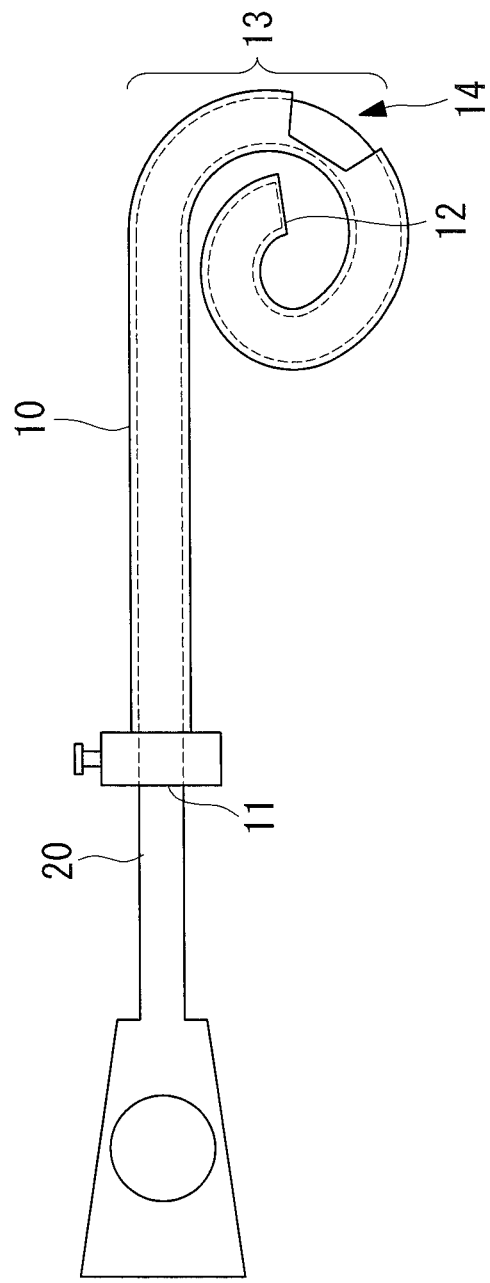

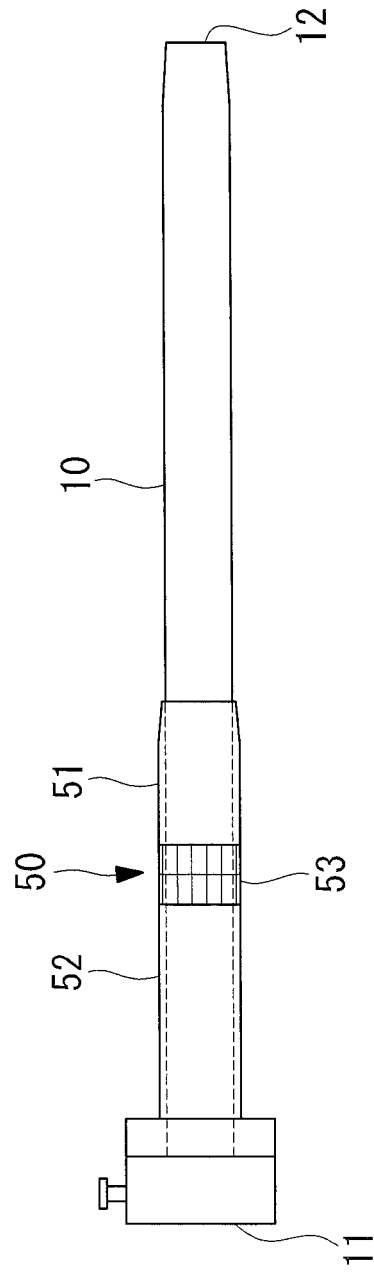
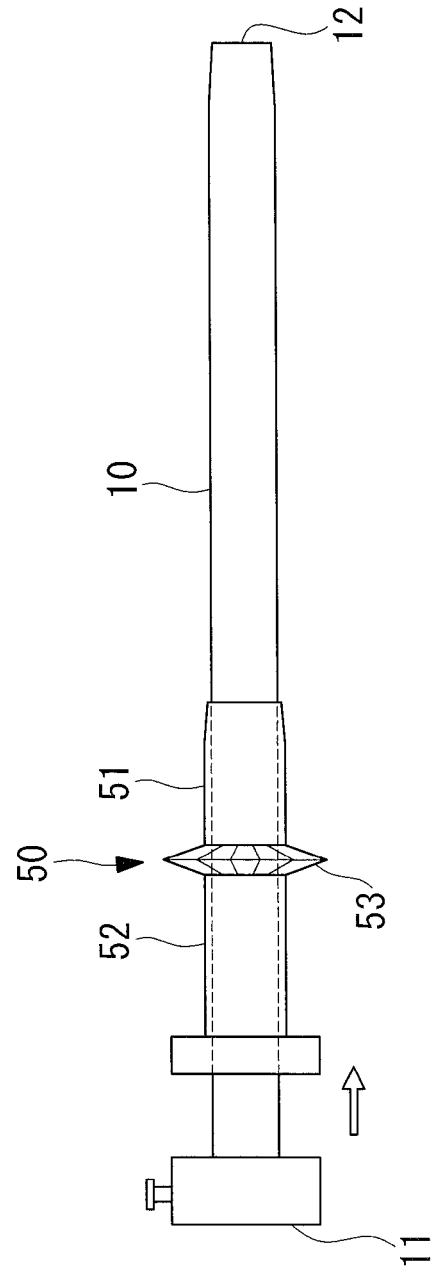

GUIDE SHEATH AND GUIDE SHEATH SYSTEM

CROSS-REFERENCE TO RELATED APPLICATIONS

This is a continuation of International Application PCT/JP2012/060593, with an international filing date of Apr. 19, 2012, which is hereby incorporated by reference herein in its entirety. This application is based on Japanese Patent Application No. 2011-098631, the contents of which are incorporated herein by reference.

TECHNICAL FIELD

The present invention relates to guide sheaths that guide insertion sections of medical devices into body cavities, and to guide sheath systems equipped with the same.

BACKGROUND ART

In the related art, there is a known guide sheath used in the medical field for guiding an insertion section of a medical device, such as an endoscope, into a body cavity when inserting the insertion section into the body cavity (for example, see Patent Literature 1).

CITATION LIST

Patent Literature

{PTL 1}
Japanese Unexamined Patent Application, Publication No. 2003-102843

SUMMARY OF INVENTION

Technical Problem

With the guide sheath disclosed in Patent Literature 1, the distal end of the guide sheath may sometimes come out of the body cavity while the insertion section is being manipulated within the body cavity. In that case, since it is not possible to insert another insertion section into the body cavity, a process for reinserting the guide sheath into the body cavity is necessary, thus requiring labor and time for that process.

The present invention provides a guide sheath and a guide sheath system that are prevented from coming out of a body cavity so as to allow for safe operation.

Solution to Problem

According to a first aspect of the present invention, a tubular guide sheath that guides an insertion section of a medical device to be inserted into a body cavity includes a base-end opening that is provided at a base end of the guide sheath and into which the insertion section is inserted; a distal-end opening that is provided at a distal end of the guide sheath; a flexible bent section that is provided at the distal end of the guide sheath and is elastically bent; and an exit opening that is provided in an outer side surface of the bent section and from which the insertion section extends out.

According to the first aspect of the present invention, for example, in order to insert the insertion section of the medical device, such as an endoscope, into the body cavity, such as a pericardial cavity, the pericardium is first pierced with a puncture needle from the skin surface, and a guide wire is then inserted into the pericardial cavity. Subsequently, the guide sheath and a dilator are inserted together into the pericardial cavity along the guide wire. Then, the dilator is pulled out so that the distal end of the guide sheath is disposed within the pericardial cavity and the base end of the guide sheath is disposed outside the body cavity. In this state, the insertion section is inserted through the base-end opening of the guide sheath so that the insertion section extending through the guide sheath extends out from the exit opening, whereby the insertion section is inserted into the pericardial cavity.

In this case, since the bent section that is elastically bent is flexible, the bent section is deformed into a straight shape by inserting a rod-shaped dilator from the base-end opening to the distal-end opening along the dilator. Thus, the guide sheath and the dilator can be readily inserted into the pericardial cavity along the guide wire.

By pulling out the dilator from the guide sheath, the bent section, which was elastically bent to begin with, deforms into its original shape (i.e., bent shape). Thus, the bent section becomes engaged with the inner side of the pericardium, whereby the guide sheath is prevented from coming out of the pericardial cavity. In this state, the insertion section is inserted through the base-end opening of the guide sheath, so that the insertion section extending through the guide sheath engaged with the inner side of the pericardium extends out from exit opening, whereby the insertion section is inserted into the pericardial cavity. Thus, the endoscope can be manipulated within the pericardial cavity without the guide sheath coming out of the pericardium, thereby allowing for stable endoscopic observation and treatment within the pericardial cavity.

Because the exit opening from which the insertion section extends out is formed in the outer side surface of the bent section, the endoscope can be readily brought close to an observation site within the pericardial cavity, thereby allowing for improved manipulability of the endoscope within the pericardial cavity.

In the above aspect, the exit opening in the bent section may be oriented toward the distal end of the guide sheath in an axial direction thereof.

Accordingly, the insertion section of the medical device, such as an endoscope, can extend out from the exit opening, in the bent section, which is oriented toward the distal end of the guide sheath in the axial direction thereof (e.g., about 0° to 15° relative to the insertion direction of the insertion section). Thus, the endoscope insertion section can be readily brought close to an observation site that is located within the body cavity, such as a pericardial cavity, toward the distal end of the guide sheath in the insertion direction, thereby facilitating observation and treatment of the observation site.

In the above aspect, the exit opening in the bent section may be oriented in a direction that intersects an axis of the guide sheath.

Accordingly, the insertion section of the medical device, such as an endoscope, can extend out from the exit opening, in the bent section, which is oriented in the direction that intersects the axis of the guide sheath (e.g., 75° to 115° relative to the insertion direction of the insertion section). Thus, the endoscope insertion section can be readily brought close to an observation site that is located within the body cavity, such as a pericardial cavity, in a direction substantially orthogonal to (i.e., that intersects) the insertion direction of the guide sheath, thereby facilitating observation and treatment of the observation site.

In the above aspect, the exit opening in the bent section may be oriented toward the base end of the guide sheath in an axial direction thereof.

Accordingly, the insertion section of the medical device, such as an endoscope, can extend out from the exit opening, in the bent section, which is oriented toward the base end of the guide sheath in the axial direction (e.g., 165° to 195° relative to the insertion direction of the insertion section). Thus, the endoscope insertion section can be readily brought close to an observation site that is located within the body cavity, such as a pericardial cavity, toward the base end of the guide sheath in the insertion direction, thereby facilitating observation and treatment of the observation site.

In the above aspect, the guide sheath may further include a deforming unit, provided in the guide sheath, for deforming the bent section into a straight shape.

By deforming the bent section into a straight shape by means of the deforming unit, the guide sheath and the dilator can be readily inserted into the body cavity, such as a pericardial cavity, without using a guide wire. Furthermore, after pulling out the insertion section of, for example, an endoscope from the guide sheath, the bent section is deformed into a straight shape by means of the deforming unit so that the bent section can be disengaged from the inner side of the pericardium without having to insert the dilator, whereby the guide sheath can be readily pulled out from the body cavity, such as a pericardial cavity.

In the above aspect, the deforming unit may be a tow wire that extends through an outer side of the bent section within the guide sheath and that is connected to the distal end of the guide sheath.

Accordingly, the bent section can be deformed into a straight shape by pulling the tow wire extending through the outer side of the bent section and connected to the distal end of the guide sheath. Thus, as described above, the guide sheath can be readily pulled out from the body cavity. Furthermore, by adjusting the pulling distance of the tow wire, the bent section can be deformed into a desired shape, so that the endoscope can be readily brought close to various observation sites in the body cavity, such as a pericardial cavity, thereby facilitating observation and treatment of each observation site.

In the above aspect, a separator that separates the bent section into an outer side and an inner side may be provided within the guide sheath and may extend in an axial direction thereof from the base-end opening to the distal-end opening.

Accordingly, when the guide sheath is to be inserted into the body cavity or is to be pulled out from the body cavity, the bent section can be deformed into a straight shape by inserting the dilator through the inner side of the bent section. Thus, as described above, the guide sheath can be readily inserted into and pulled out from the body cavity.

On the other hand, when inserting the insertion section of, for example, an endoscope into the body cavity, the insertion section is inserted through the outer side of the bent section so that the insertion section can extend out from the exit opening and be inserted into the pericardial cavity in a state where the bent section is maintained in a bent shape, that is, in a state where the bent section is engaged with the inner side of the pericardium. Thus, the endoscope can be manipulated within the pericardial cavity without the guide sheath coming out of the pericardium, thereby allowing for stable endoscopic observation and treatment within the pericardial cavity.

In the above aspect, the guide sheath may further include an expanding mechanism that is provided at the base end of the guide sheath and that expands in a radially outward direction of the guide sheath.

Accordingly, in addition to the bent section being engaged with the inner side of the pericardium, the expanding mechanism can be engaged with the inner wall of the body cavity by expanding the expanding mechanism in the radially outward direction of the guide sheath. Thus, the guide sheath can be more reliably prevented from coming out of the body cavity.

In the above aspect, the guide sheath may further include a strap that is provided at the base end of the guide sheath and that secures the guide sheath to a body surface.

Accordingly, in addition to the bent section being engaged with the inner side of the pericardium, the guide sheath can be secured to the body surface by using the strap. Thus, the guide sheath can be more reliably prevented from coming out of the body cavity.

In the above aspect, the guide sheath may further include a rotation maintaining mechanism that maintains the guide sheath in a rotated state about an axis thereof.

By rotating the guide sheath about its axis, the pericardium is pressed upward by the bent section, whereby a gap can be formed in the pericardial cavity. In this state, the guide sheath is maintained in position by the rotation maintaining mechanism in the state where the gap is formed in the pericardial cavity, thereby allowing for improved ease of use when performing observation and treatment in the pericardial cavity.

In the above aspect, the guide sheath may further include an air-sealing unit at the base end of the guide sheath.

In the above aspect, the guide sheath may be radiopaque.

According to a second aspect of the present invention, a guide sheath system includes the guide sheath according to the first aspect; a rod-shaped dilator that is inserted into the guide sheath; and a guide wire that is inserted into the guide sheath and guides the dilator through the guide sheath.

Because this guide sheath system is equipped with the aforementioned guide sheath, an endoscope can be manipulated within the pericardial cavity without the guide sheath coming out of the pericardium, thereby allowing for stable endoscopic observation and treatment within the pericardial cavity.

Advantageous Effects of Invention

The present invention is advantageous in that it prevents the guide sheath from coming out of the body cavity so as to allow for safe operation.

BRIEF DESCRIPTION OF DRAWINGS

FIG. 13 illustrates a state where the dilator is inserted into the guide sheath in FIG. 1.

FIG. 14 illustrates a state just before the guide sheath in FIG. 1 is pulled out from the pericardial cavity, in accordance with a first modification.

FIG. 45 schematically illustrates the configuration of a guide sheath according to a ninth modification.

FIG. 46 illustrates a state where an expanding mechanism in FIG. 45 is actuated.

DESCRIPTION OF EMBODIMENTS

A guide sheath 10 and a guide sheath system 1 equipped with the same according to an embodiment of the present invention will be described below with reference to the drawings.

Figure 1:
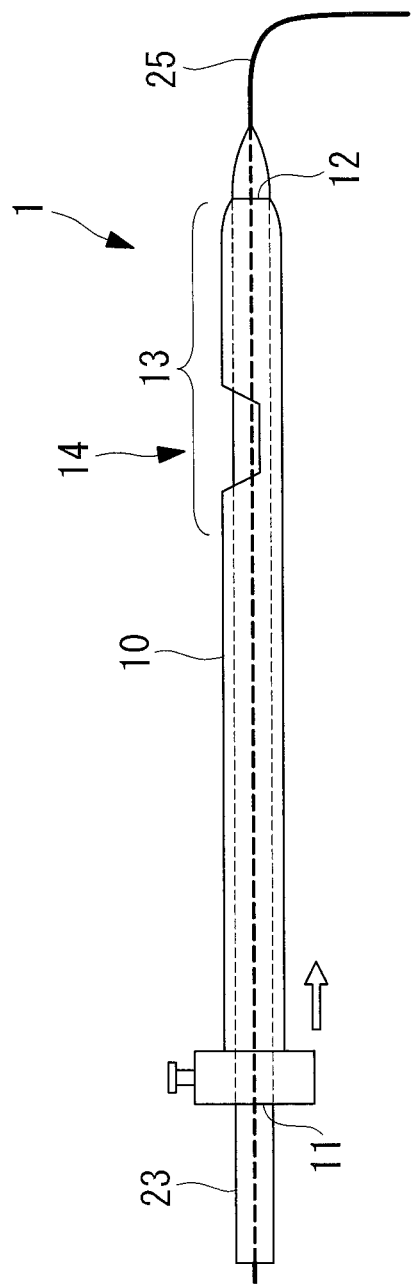
FIG. 1 schematically illustrates the configuration of a guide sheath system according to an embodiment of the present invention.

As shown in FIG. 1, the guide sheath system 1 according to this embodiment includes a tubular guide sheath 10 that guides, for example, an insertion section of a medical device to be inserted into a body cavity, a rod-shaped dilator 23 that is inserted into the guide sheath 10, and a guide wire 25 that is inserted into the guide sheath 10.

Figure 2:
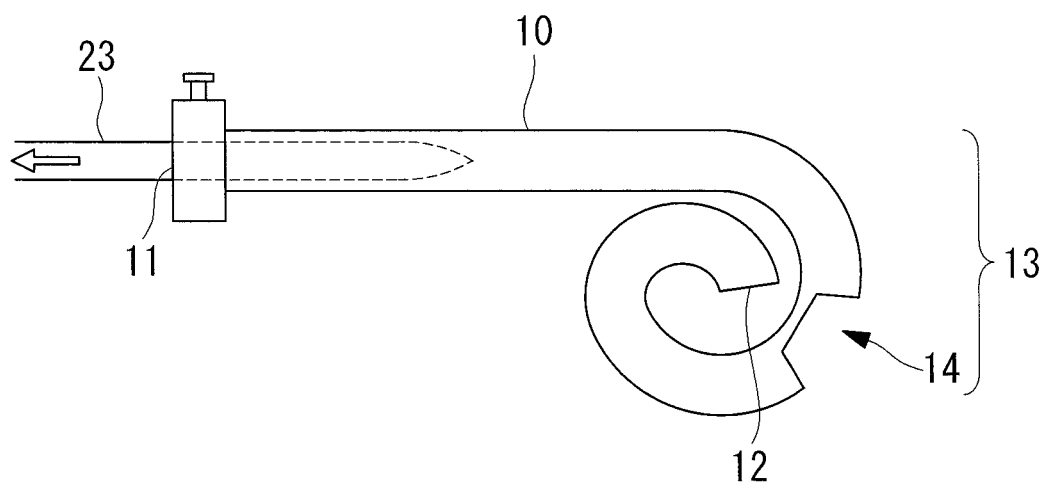
FIG. 2 illustrates a state where a dilator is being pulled out from a guide sheath in FIG. 1.

As shown in FIG. 2, the guide sheath 10 includes a base-end opening 11 provided at the base end of the guide sheath 10, a distal-end opening 12 provided at the distal end of the guide sheath 10, a bent section 13 provided at the distal end of the guide sheath 10, and an exit opening 14 formed in an outer side surface (i.e., radially outer side surface) of the bent section 13. The following description relates to an example where an endoscope insertion section 20 (see FIG. 3) is inserted into the pericardial cavity between the heart and the pericardium by using the guide sheath 10 according to this embodiment.

Figure 3:
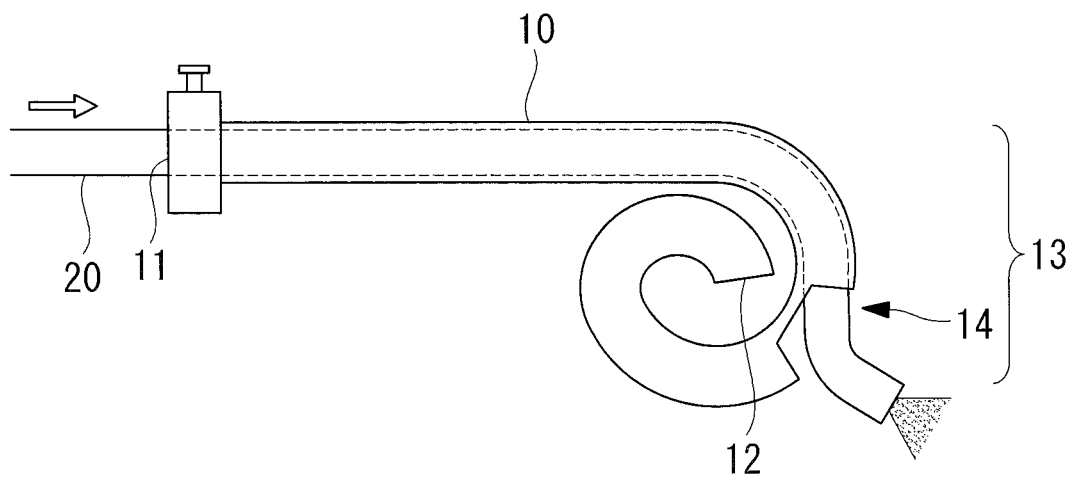
FIG. 3 illustrates a state where an insertion section is being inserted into the guide sheath in FIG. 1.

The guide sheath 10 has a tubular shape and is configured to guide the endoscope insertion section 20 into the pericardial cavity between the heart and the pericardium, as shown in FIG. 3. Specifically, the distal end of the guide sheath 10 is disposed within the pericardial cavity, whereas the base end of the guide sheath 10 is disposed outside the body cavity, whereby the endoscope insertion section 20 can be guided into the pericardial cavity from outside the body cavity.

The base-end opening 11 is an opening provided at the base end of the guide sheath 10. As shown in FIGS. 1 and 3, the endoscope insertion section 20, the dilator 23, and the guide wire 25 are inserted through the base-end opening 11.

The distal-end opening 12 is an opening provided at the distal end of the guide sheath 10. As shown in FIG. 1, the dilator 23 and the guide wire 25 extend out from the distal-end opening 12.

As shown in FIG. 2, the distal end of the guide sheath 10 is provided with the bent section 13, which is flexible and is elastically bent.

The exit opening 14 is formed in the outer side surface (i.e., radially outer side surface) of the bent section 13. As shown in FIG. 3, the endoscope insertion section 20 extends out from the exit opening 14.

The dilator 23 is a rod-shaped member that is inserted into the guide sheath 10 through the base-end opening 11. The dilator 23 is inserted into the guide sheath 10 along the guide wire 25, which is set within the guide sheath 10 in advance. The dilator 23 has a tapered end such that the dilator 23 is capable of penetrating the pericardium while expanding a hole therein. In order to minimize invasiveness to biological tissue within the body cavity, the dilator 23 and the guide sheath 10 are desirably composed of biocompatible resin. Furthermore, at least the distal ends of the dilator 23 and the guide sheath 10 need to be radiopaque so that the positions of the guide sheath 10 and the dilator 23 can be confirmed in a radioscopic image.

The guide wire 25 guides the dilator 23 from the base-end opening 11 to the distal-end opening 12 of the guide sheath 10. The guide wire 25 may be elastically bent into a shape similar to that of the bent section 13 of the guide sheath 10 so that the guide wire 25 can readily guide the dilator 23 through the guide sheath 10.

The following description relates to the operation performed when inserting the guide sheath 10 into the pericardial cavity by using the guide sheath system 1 having the above-described configuration.

Figure 4:
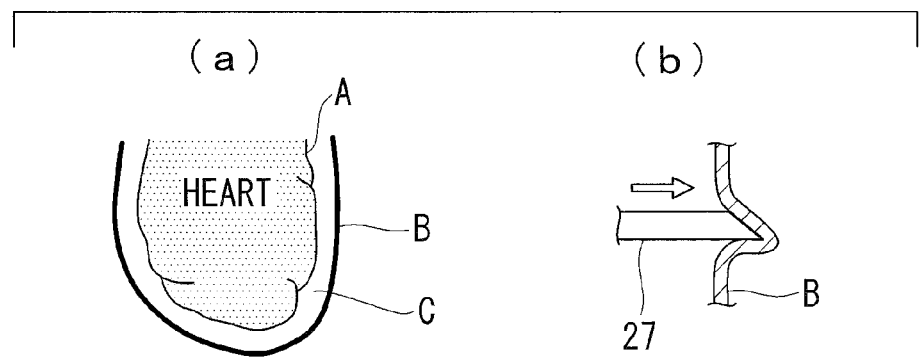
FIG. 4 illustrates a state where the guide sheath in FIG. 1 is being inserted into a pericardial cavity and includes (*a*) showing a state within the pericardial cavity and (*b*) showing a state where the pericardium is being pierced with a puncture needle.

In order to insert the endoscope insertion section 20 into the pericardial cavity C shown in FIG. 4(a), the pericardium B is first pierced with a puncture needle 27 from the skin surface, as shown in FIG. 4(b).

Figure 5:
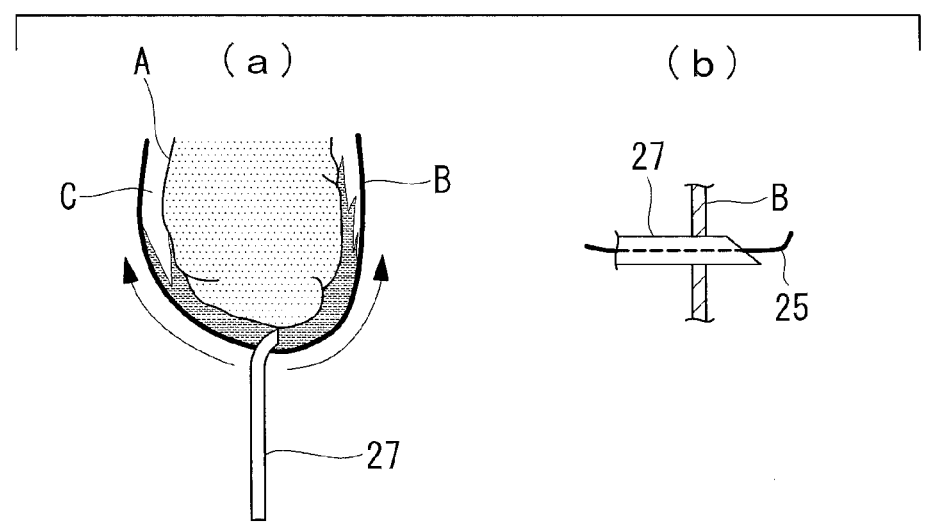
FIG. 5 illustrates a state where the guide sheath in FIG. 1 is inserted into the pericardial cavity and includes (*a*) showing a state where a contrast agent is injected into the pericardial cavity and (*b*) showing a state where the puncture needle has penetrated through the pericardium.

Subsequently, as shown in FIG. 5(a), a contrast agent is injected into the pericardial cavity C through the puncture needle 27. The contrast agent spreads throughout the pericardial cavity C so that it can be confirmed from a radioscopic image that the needle tip has entered the pericardial cavity C. In this state, the guide wire 25 is inserted into the pericardial cavity C through the puncture needle 27, as shown in FIG. 5(b).

Figure 6:
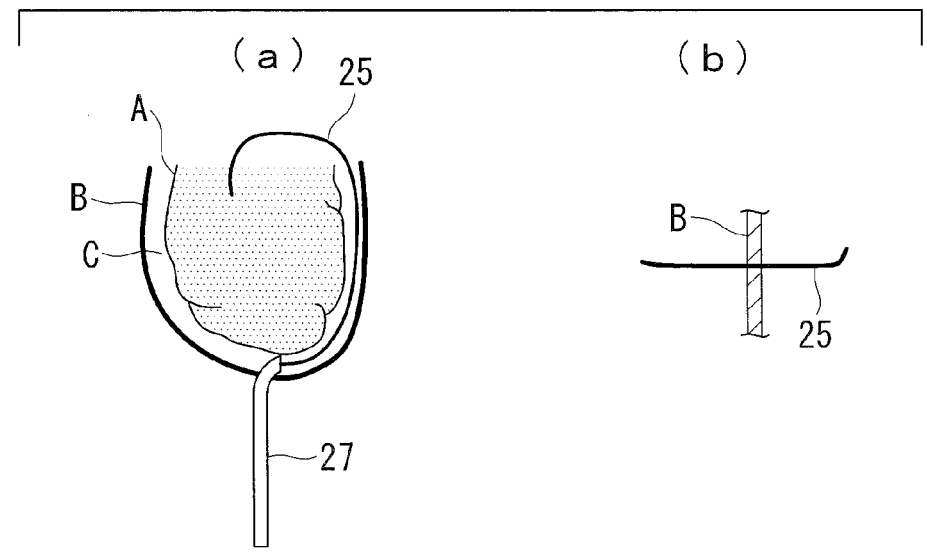
FIG. 6 illustrates a state where the guide sheath in FIG. 1 is inserted into the pericardial cavity and includes (*a*) showing a state where a guide wire is inserted into the pericardial cavity and (*b*) showing a state where the puncture needle has been pulled out from the pericardium.

Subsequently, as shown in FIG. 6(a), the guide wire 25 is inserted further into the pericardial cavity C. Then, the puncture needle 27 is pulled out from the pericardium B, as shown in FIG. 6(b).

Figure 7:
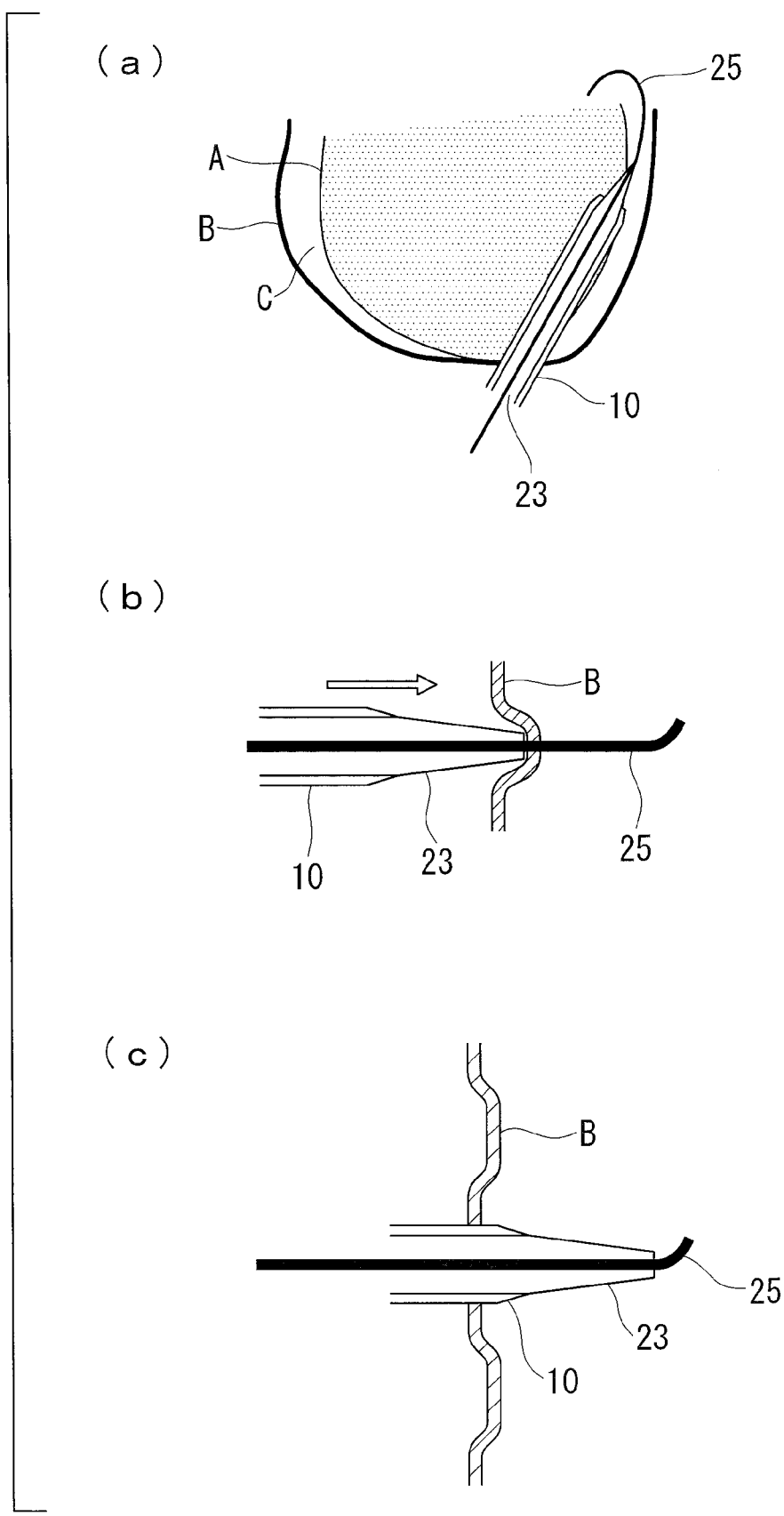
FIG. 7 illustrates a state where the guide sheath in FIG. 1 is inserted into the pericardial cavity and includes (a) showing a state where the guide sheath is inserted into the pericardial cavity, (b) showing a state where the dilator is being inserted through the pericardium, and (c) showing a state where the guide sheath is inserted through the pericardium.

Subsequently, as shown in FIGS. 7(b) and 7(c), the guide sheath 10 and the dilator 23 are inserted together into the pericardial cavity C along the guide wire 25. In this case, the elastically bent flexible bent section 13 of the guide sheath 10 is deformed into a straight shape along the dilator 23 due to the rod-shaped dilator 23 extending from the base-end opening 11 to the distal-end opening 12, as shown in FIG. 1. Thus, the guide sheath 10 and the dilator 23 can be readily inserted into the pericardial cavity C along the guide wire 25. Accordingly, as shown in FIG. 7(a), the distal ends of the guide sheath 10 and the dilator 23 are disposed within the pericardial cavity C.

Subsequently, the dilator 23 is pulled out from the guide sheath 10 so that the distal end of the guide sheath 10 is disposed within the pericardial cavity C and the base end of the guide sheath 10 is disposed outside the body cavity.

In this case, since the dilator 23 is pulled out from the guide sheath 10, the bent section 13 of the guide sheath 10 deforms into its original shape (i.e., bent shape), as shown in FIG. 2. Thus, the bent section 13 of the guide sheath 10 becomes engaged with the inner side of the pericardium B, whereby the guide sheath 10 is prevented from coming out of the pericardial cavity C.

In this state, the endoscope insertion section 20 is inserted through the base-end opening 11 of the guide sheath 10, as shown in FIG. 3, so that the endoscope insertion section 20 extending through the guide sheath 10 engaged with the inner side of the pericardium B extends out from exit opening 14, whereby the endoscope insertion section 20 is inserted into the pericardial cavity C. Thus, the endoscope can be manipulated within the pericardial cavity C without the guide sheath 10 coming out of the pericardium B, thereby allowing for stable endoscopic observation and treatment within the pericardial cavity C.

Because the exit opening 14 from which the endoscope insertion section 20 extends out is formed in the outer side surface of the bent section 13, the endoscope insertion section 20 can be readily brought close to an observation site within the pericardial cavity C, thereby allowing for improved manipulability of the endoscope within the pericardial cavity C.

Figure 8:
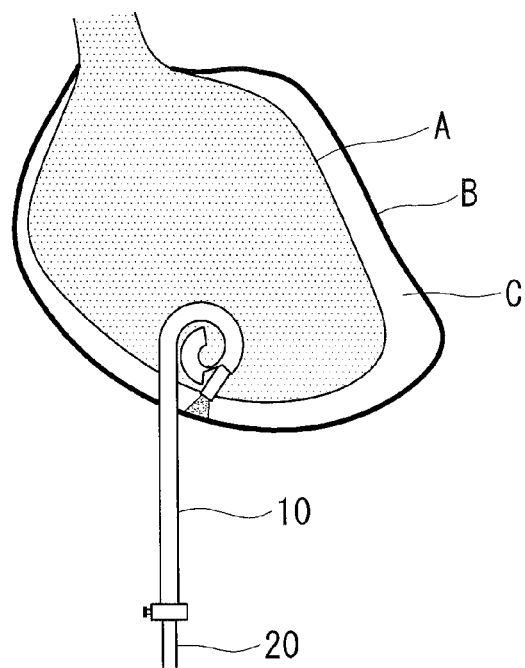
FIG. 8 illustrates a state where the insertion section inserted into the pericardial cavity by using the guide sheath in FIG. 1 is oriented toward the base end thereof.

In this case, as shown in FIG. 8, the exit opening 14 in the bent section 13 of the guide sheath 10 may be oriented toward the base end of the guide sheath 10 in the axial direction (e.g., 135° to 215° relative to the insertion direction of the insertion section 20).

Accordingly, the endoscope insertion section 20 can extend out from the exit opening 14 formed in the bent section 13 and oriented toward the base end of the guide sheath 10 in the axial direction. Thus, the endoscope insertion section 20 can be readily brought close to an observation site that is located within the pericardial cavity C toward the base end of the guide sheath 10 in the insertion direction, thereby facilitating the observation and treatment of the observation site. This is advantageous in a case where, for example, puncture needles 27 are to be observed in the pericardial cavity C when multiple guide sheaths are inserted into the pericardial cavity C. Moreover, this is also advantageous when observing the apex of the heart.

Figure 9:
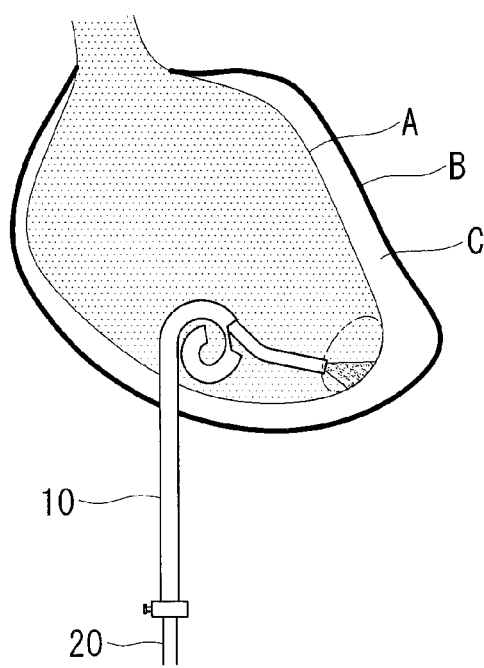
FIG. 9 illustrates a state where the insertion section inserted into the pericardial cavity by using the guide sheath in FIG. 1 is oriented in a direction intersecting the axis thereof.

Furthermore, as shown in FIG. 9, the exit opening 14 in the bent section 13 of the guide sheath 10 may be oriented in a direction that intersects the axis of the guide sheath (e.g., 45° to 135° relative to the insertion direction of the insertion section 20).

Accordingly, the endoscope insertion section 20 can extend out from the exit opening 14 formed in the bent section 13 and oriented in the direction that intersects the axis of the guide sheath 10. Thus, the endoscope insertion section 20 can be readily brought close to an observation site that is located within the pericardial cavity C in a direction substantially orthogonal to (i.e., that intersects) the insertion direction of the guide sheath 10, thereby facilitating the observation and treatment of the observation site. This is advantageous when, for example, observing affected areas in the sidewall of the left ventricle, the posterior wall of the left ventricle, and the apex of the heart.

Figure 10:
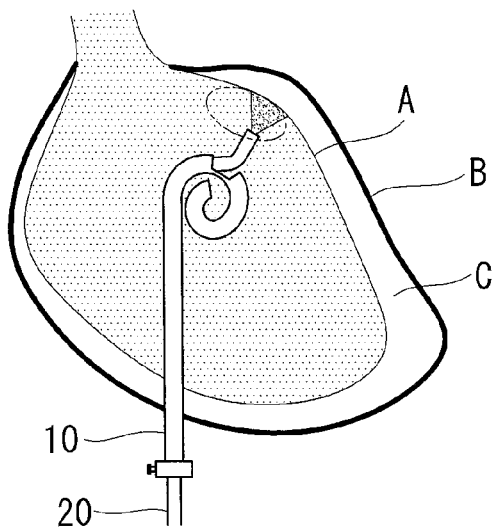
FIG. 10 illustrates a state where the insertion section inserted into the pericardial cavity by using the guide sheath in FIG. 1 is oriented toward the distal end thereof.

Furthermore, as shown in FIG. 10, the exit opening 14 in the bent section 13 of the guide sheath 10 may be oriented toward the distal end of the guide sheath 10 in the axial direction (e.g., 0° to 45° relative to the insertion direction of the insertion section 20).

Accordingly, the endoscope insertion section 20 can extend out from the exit opening 14 formed in the bent section 13 and oriented toward the distal end of the guide sheath 10 in the axial direction. Thus, the endoscope insertion section 20 can be readily brought close to an observation site that is located within the pericardial cavity C toward the distal end of the guide sheath 10 in the insertion direction, thereby facilitating the observation and treatment of the observation site. This is advantageous when, for example, observing affected areas in the auricle and the atrium. Moreover, this is also advantageous when approaching the rear side or a side surface of the heart by looping the insertion section around the base of the heart.

By selectively using guide sheaths 10 with exit openings 14 set at different positions (orientations) in accordance with observation sites, the endoscope insertion section 20 can be readily brought close to an observation site without having to move the endoscope insertion section 20 forward or rearward, to bend the endoscope insertion section 20, or to rotate the endoscope insertion section 20. Thus, the efficiency of the observation and treatment procedures can be improved, and the load on the human body can be reduced.

Furthermore, multiple exit openings 14 may be provided in a single guide sheath 10, such that the exit opening 14 from which the endoscope insertion section 20 extends out may be selected from among the multiple exit openings 14 in accordance with the observation site.

Next, the operation performed when pulling out the guide sheath 10 from the pericardial cavity C by using the guide sheath system 1 according to this embodiment will be described below.

Figure 11:
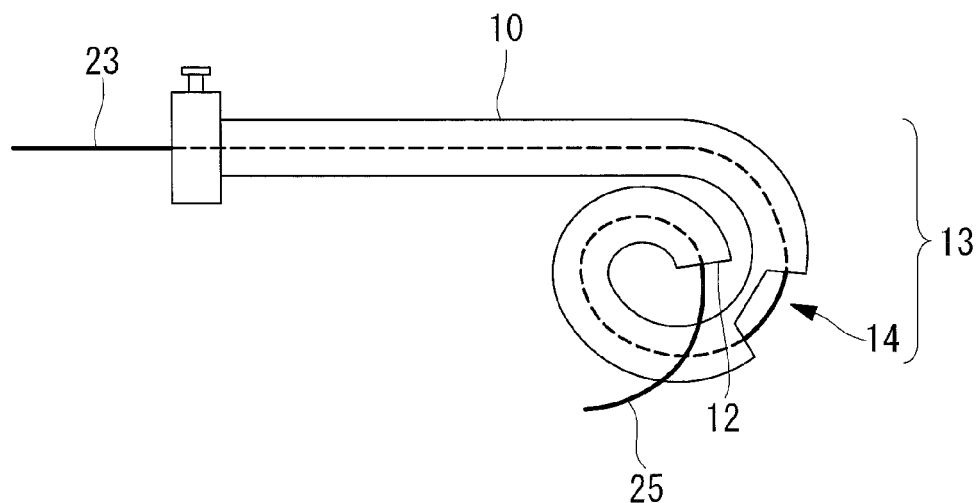
FIG. 11 illustrates a state just before the guide sheath in FIG. 1 is pulled out from the pericardial cavity.

First, as shown in FIG. 11, the guide wire 25 is set within the guide sheath 10 such that the guide wire 25 extends therethrough from the base-end opening 11 to the distal-end opening 12. Alternatively, the guide wire 25 may be elastically bent into a shape similar to that of the bent section 13 before the guide wire 25 is inserted into the guide sheath 10.

Figure 12:
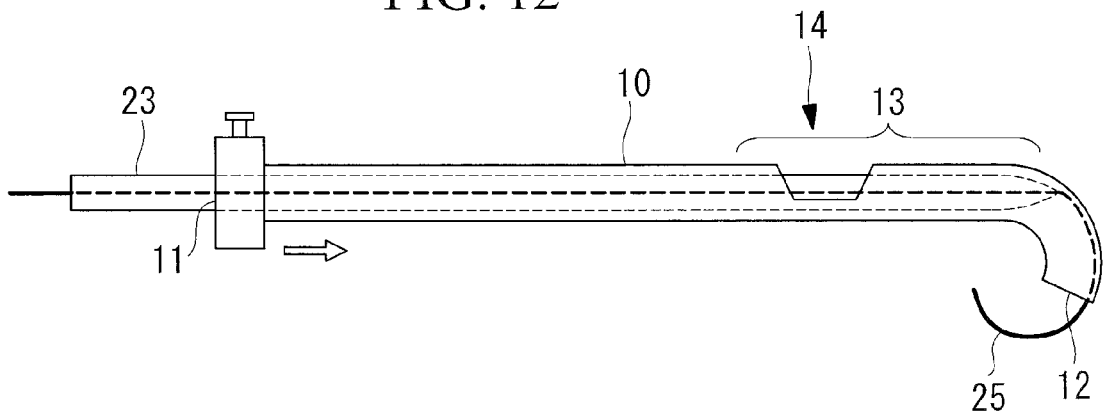
FIG. 12 illustrates a state where the dilator is being inserted into the guide sheath in FIG. 1.

Subsequently, as shown in FIG. 12, the rod-shaped dilator 23 is inserted into the guide sheath 10 from the base-end opening 11 to the distal-end opening 12 along the guide wire 25. Thus, the bent section 13 of the guide sheath 10 is deformed into a straight shape along the rod-shaped dilator 23, as shown in FIG. 13. Consequently, the guide sheath 10 and the dilator 23 can be readily pulled out from the pericardial cavity C. Accordingly, the efficiency of the procedure for pulling out the guide sheath 10 from the pericardial cavity C can be improved, and the load on the human body (pericardium B) can be reduced.

[First Modification]

Figure 15:
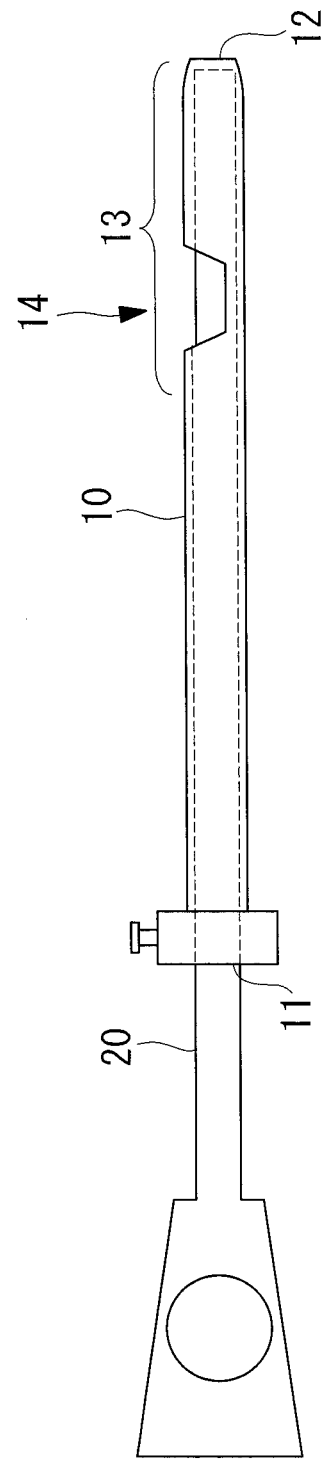
FIG. 15 illustrates a state where the guide sheath is straightened out by the insertion section in FIG. 14.

As a first modification of the guide sheath 10 according to this embodiment, a bending mechanism of the endoscope insertion section 20 may be used in the procedure for pulling out the guide sheath 10 from the pericardial cavity C, as shown in FIGS. 14 and 15.

Specifically, as shown in FIG. 14, the endoscope insertion section 20 is first inserted into the guide sheath 10 from the base-end opening 11 to the distal-end opening 12 while the endoscope insertion section 20 is bent in accordance with the shape of the bent section 13 of the guide sheath 10.

Then, as shown in FIG. 15, the bending mechanism of the endoscope insertion section 20 is actuated so as to deform the bent section 13 of the guide sheath 10 into a straight shape. Thus, the guide sheath 10 and the endoscope insertion section 20 can be readily pulled out from the pericardial cavity C. Accordingly, the efficiency of the procedure for pulling out the guide sheath 10 from the pericardial cavity C can be improved, and the load on the human body (pericardium B) can be reduced. In addition, the aforementioned procedure can be performed while observing the procedure with the endoscope insertion section 20, whereby the procedure can be performed more efficiently.

[Second Modification]

As a second modification of the guide sheath 10 according to this embodiment, a hollow catheter 29 may be used in the procedure for pulling out the guide sheath 10 from the pericardial cavity C, as shown in FIGS. 16 to 19.

Figure 16:
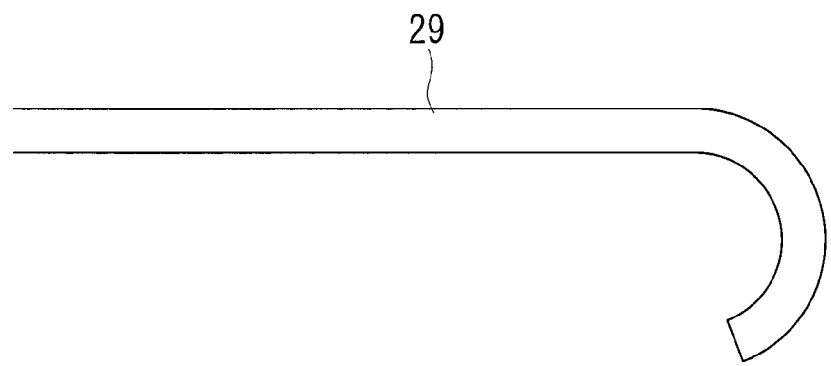
FIG. 16 illustrates a catheter used for pulling out the guide sheath in FIG. 1 from the pericardial cavity, in accordance with a second modification.
Figure 17:
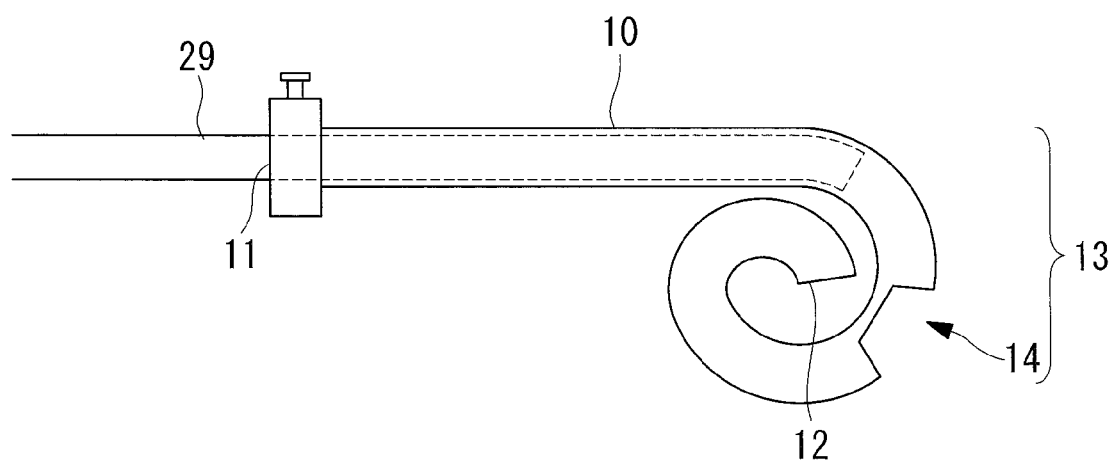
FIG. 17 illustrates a state where the catheter in FIG. 16 is being inserted into the guide sheath.
Figure 18:
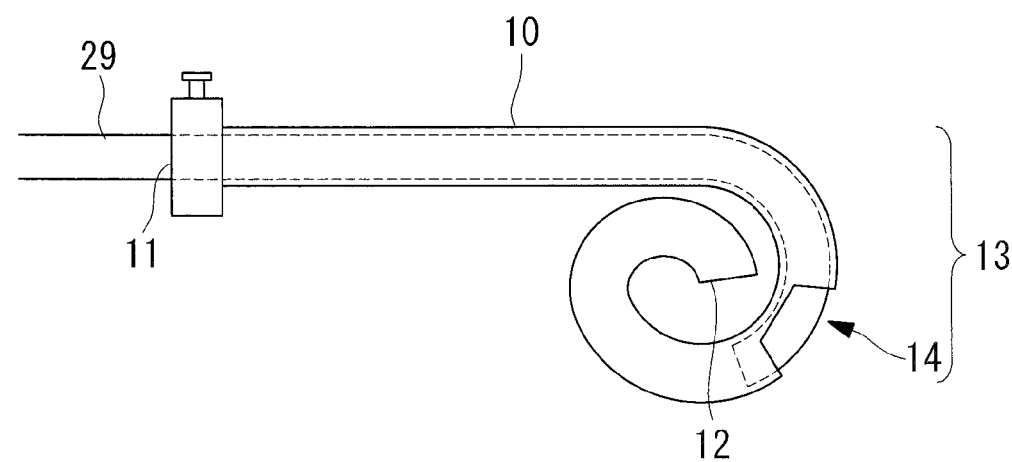
FIG. 18 illustrates a state where the catheter in FIG. 16 is inserted into the guide sheath.

Specifically, the hollow catheter 29, which is elastically bent into a shape similar to that of the bent section 13 of the guide sheath 10, as shown in FIG. 16, is inserted into the guide sheath 10 from the base-end opening 11 to the distal-end opening 12, as shown in FIGS. 17 and 18.

Figure 19:
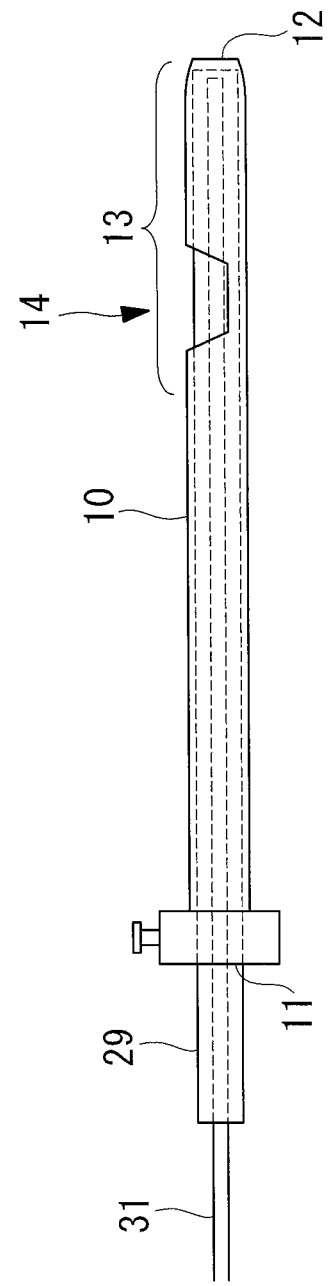
FIG. 19 illustrates a state where the guide sheath is straightened out by the catheter in FIG. 16.

Subsequently, as shown in FIG. 19, a linear wire 31 is inserted into (the hollow section of) the catheter 29 so as to deform the catheter 29 and the bent section 13 of the guide sheath 10 into a straight shape. Thus, the guide sheath 10 and the catheter 29 can be readily pulled out from the pericardial cavity C. Accordingly, the efficiency of the procedure for pulling out the guide sheath 10 from the pericardial cavity C can be improved, and the load on the human body (pericardium B) can be reduced.

[Third Modification]

As a third modification of this embodiment, the guide sheath 10 may be provided with a tow wire or tow wires 33, as shown in FIGS. 20 to 23.

Figure 20:
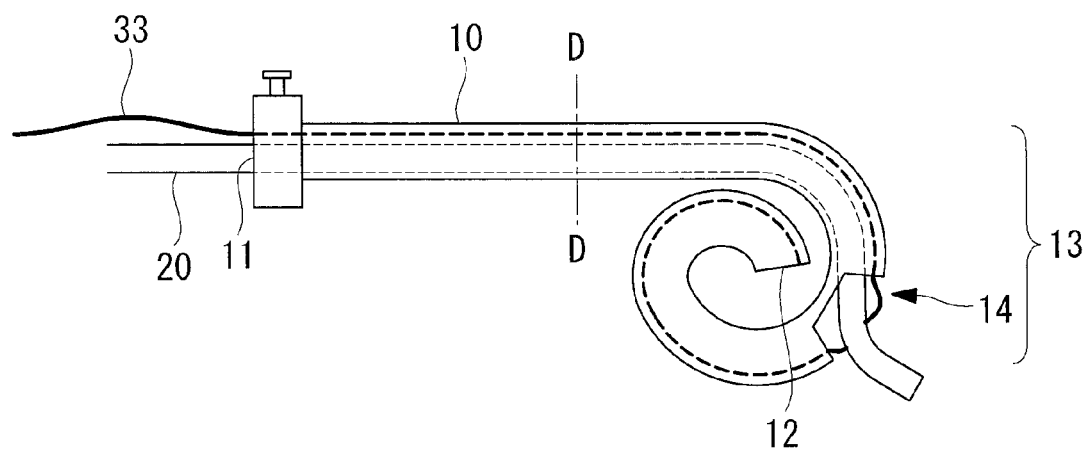
FIG. 20 illustrates a state where the guide sheath in FIG. 1 is provided with a tow wire, in accordance with a third modification.

As shown in FIG. 20, in the guide sheath 10 according to this modification, a tow wire 33 extends through the guide sheath 10 at the outer side (i.e., radially outer side) of the bent section 13. One end of the tow wire 33 is connected to the distal end of the guide sheath 10, whereas the other end extends to the base end of the guide sheath 10.

Figure 21:
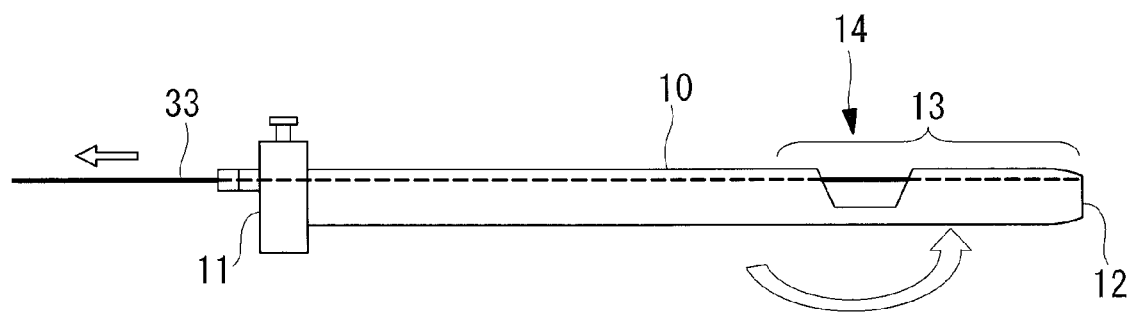
FIG. 21 illustrates a state where the guide sheath is straightened out by the tow wire in FIG. 20.

With the above-described configuration, the bent section 13 can be deformed into a straight shape by pulling the tow wire 33 toward the base end, as shown in FIG. 21. Thus, the guide sheath 10 can be readily pulled out from the pericardial cavity C. Accordingly, the efficiency of the procedure for pulling out the guide sheath 10 from the pericardial cavity C can be improved, and the load on the human body (pericardium B) can be reduced.

Furthermore, by adjusting the pulling distance of the tow wire 33, the bent section 13 of the guide sheath 10 can be deformed into a desired shape, so that the endoscope insertion section 20 can be readily brought close to various observation sites in the pericardial cavity C, thereby facilitating the observation and treatment of a target observation site.

Figure 22:
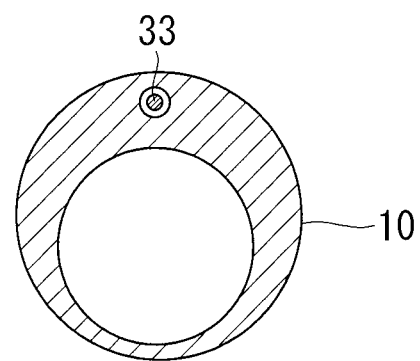
FIG. 22 is a cross-sectional view of the guide sheath in FIG. 20 (provided with a single tow wire), taken along line D-D.
Figure 23:
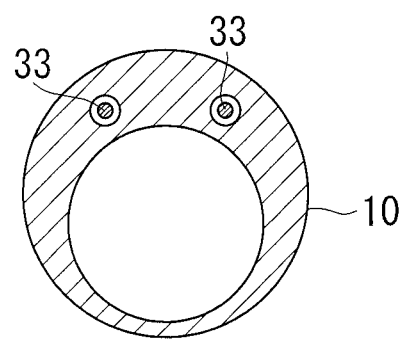
FIG. 23 is a cross-sectional view of the guide sheath in FIG. 20 (provided with multiple tow wires), taken along line D-D.

The guide sheath 10 according to this modification may have a single tow wire 33 extending through the guide sheath 10, as shown in FIG. 22, or may have multiple tow wires 33, as shown in FIG. 23. If a single tow wire 33 extends through the guide sheath 10, as shown in FIG. 22, the endoscope insertion section 20 can readily extend out from the exit opening 14 by loosening the tow wire 33.

If multiple tow wires 33 extend through the guide sheath 10, as shown in FIG. 23, the tow wires 33 may extend through positions offset from the central position (i.e., the exit position of the endoscope insertion section 20) in the circumferential direction of the exit opening 14 so that the endoscope insertion section 20 can readily extend out from the exit opening 14.

[Fourth Modification]

As a fourth modification of this embodiment, the guide sheath 10 may be provided with a tubular separator 35, as shown in FIGS. 24 to 29.

Figure 24:
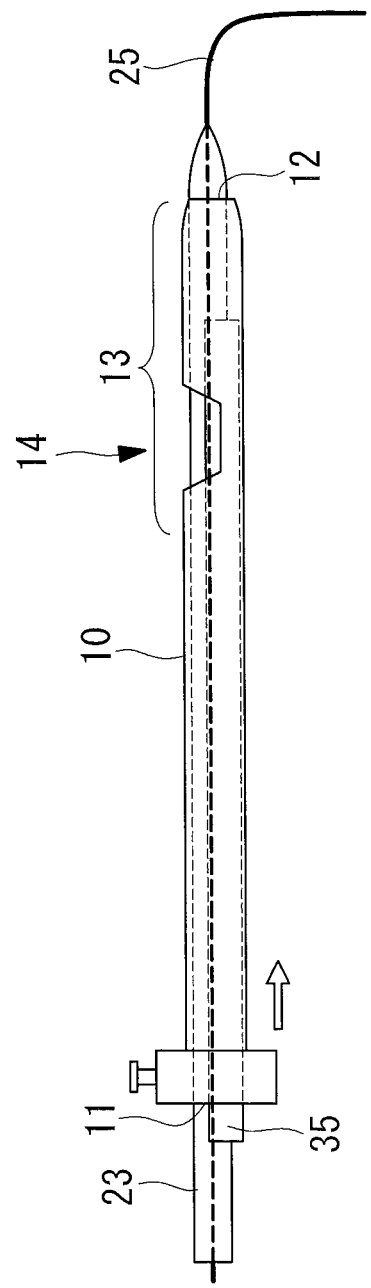
FIG. 24 illustrates a state where the guide sheath in FIG. 1 is provided with a tubular separator, in accordance with a fourth modification.
Figure 25:
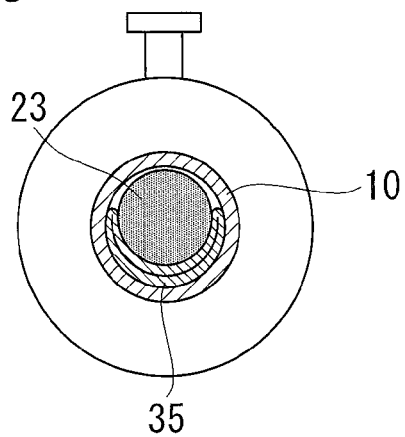
FIG. 25 is a front view of the guide sheath in FIG. 24, as viewed from the base end thereof.

As shown in FIG. 24, in the guide sheath 10 according to this modification, the separator 35 is provided in the axial direction from the base-end opening 11 to the distal-end opening 12 of the guide sheath 10. Furthermore, in a cross-sectional view of the guide sheath 10 shown in FIG. 25, the separator 35 is provided so as to separate the bent section 13 of the guide sheath 10 into an outer side and an inner side.

The separator 35 has a tubular shape and is composed of an elastic material, such as rubber. In the initial state (i.e., a state where no load is applied), the separator 35 is elastically folded into a semispherical shape toward the inner side of the bent section 13, as viewed in the cross-sectional view shown in FIG. 25.

With regard to the guide sheath 10 according to this modification, when the guide sheath 10 is to be inserted into the pericardial cavity C, the dilator 23 is inserted along the guide wire 25 through the outer side of the bent section 13 of the guide sheath 10 (i.e., the outer side of the separator 35 within the guide sheath 10), as shown in FIG. 24. Then, the guide sheath 10 and the dilator 23 are inserted together into the pericardial cavity C.

Subsequently, the dilator 23 is pulled out from the guide sheath 10 so that the distal end of the guide sheath 10 is disposed within the pericardial cavity C and the base end of the guide sheath 10 is disposed outside the body cavity.

Figure 26:
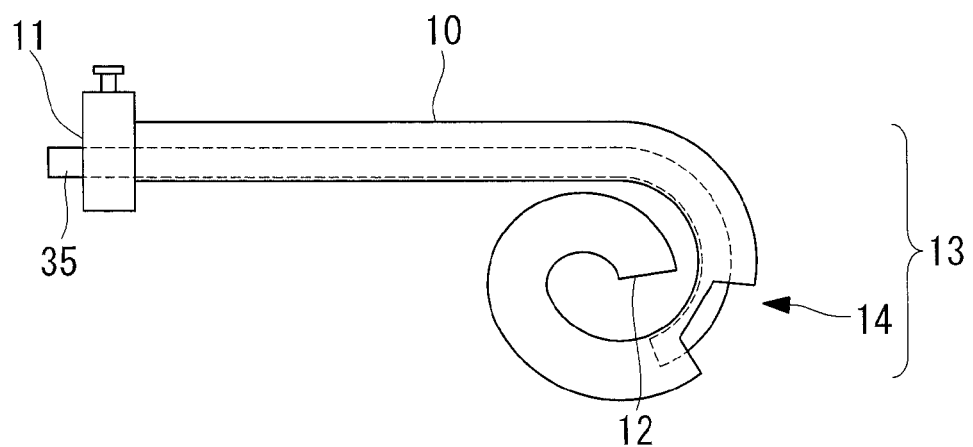
FIG. 26 is a side view of the guide sheath in FIG. 24.

In this case, since the dilator 23 is pulled out from the guide sheath 10, the bent section 13, which was elastically bent to begin with, of the guide sheath 10 deforms into its original shape (i.e., bent shape), as shown in FIG. 26.

Figure 27:
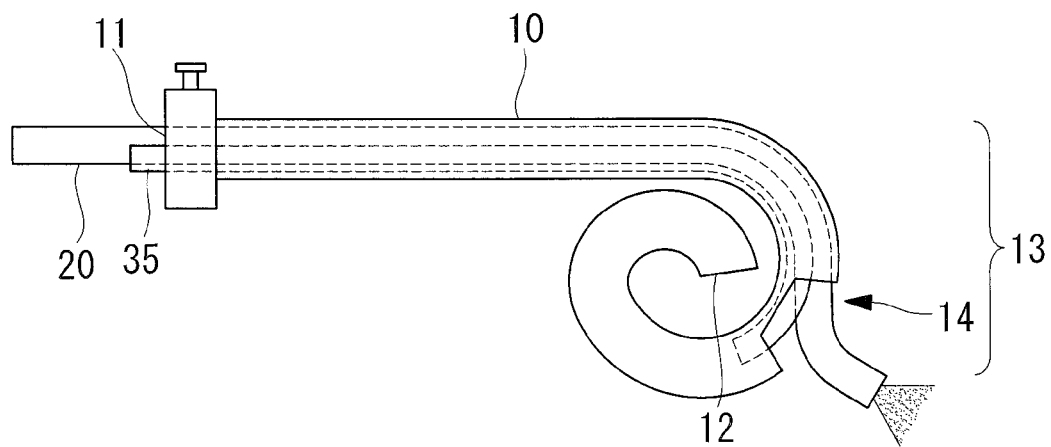
FIG. 27 illustrates a state where the insertion section is inserted into the guide sheath in FIG. 24.

In this state, the endoscope insertion section 20 is inserted through the base-end opening 11 of the guide sheath 10, as shown in FIG. 27, so that the endoscope insertion section 20 extending through the guide sheath 10 engaged with the inner side of the pericardium B extends out from the exit opening 14, whereby the endoscope insertion section 20 is inserted into the pericardial cavity C. Thus, the endoscope can be manipulated within the pericardial cavity C without the guide sheath 10 coming out of the pericardium B, thereby allowing for stable endoscopic observation and treatment within the pericardial cavity C.

Figure 28:
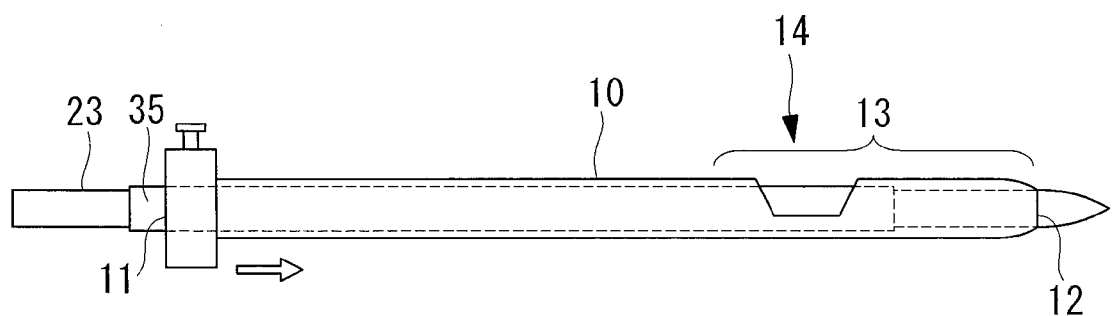
FIG. 28 illustrates a state where the dilator is inserted into the guide sheath in FIG. 24.
Figure 29:
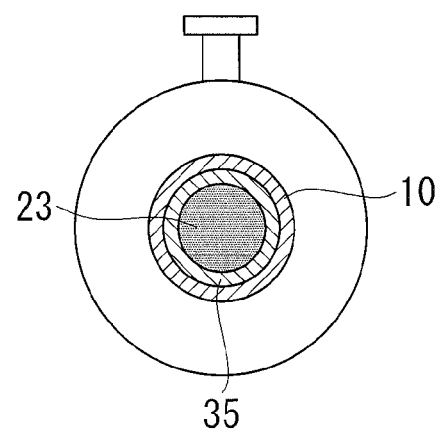
FIG. 29 is a front view of the guide sheath in FIG. 28, as viewed from the base end thereof.

On the other hand, when pulling out the guide sheath 10 from the pericardial cavity C, the dilator 23 is inserted through the inner side of the bent section 13 of the guide sheath 10 (i.e., into the separator 35 within the guide sheath 10), as shown in FIGS. 28 and 29. Thus, the dilator 23 extends through the tubular separator 35 to the distal-end opening 12 of the guide sheath 10, whereby the bent section 13 of the guide sheath 10 can be deformed into a straight shape. Consequently, the guide sheath 10 can be readily pulled out from the pericardial cavity C, whereby the efficiency of the procedure for pulling out the guide sheath 10 from the pericardial cavity C can be improved, and the load on the human body (pericardium B) can be reduced.

[Fifth Modification]

As a fifth modification of this embodiment, the guide sheath 10 may be provided with a film-like separator 36, as shown in FIGS. 30 to 34.

Figure 30:
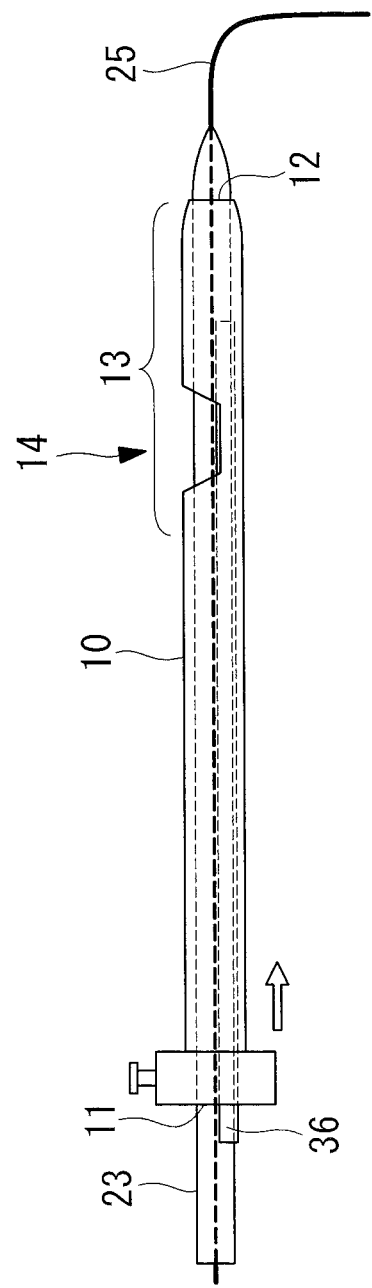
FIG. 30 illustrates a state where the guide sheath in FIG. 1 is provided with a film-like separator, in accordance with a fifth modification.
Figure 31:
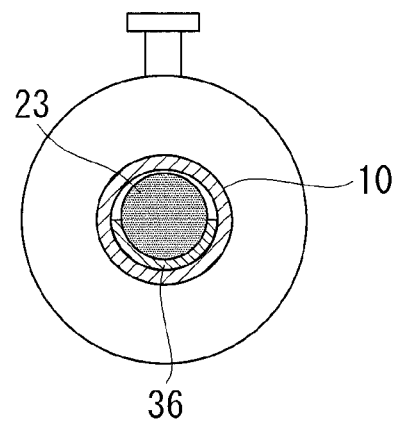
FIG. 31 is a front view of the guide sheath in FIG. 30, as viewed from the base end thereof.

As shown in FIG. 30, in the guide sheath 10 according to this modification, the separator 36 is provided in the axial direction from the base-end opening 11 to the distal-end opening 12 of the guide sheath 10. Furthermore, in a cross-sectional view of the guide sheath 10 shown in FIG. 31, the separator 36 is provided so as to separate the bent section 13 of the guide sheath 10 into an outer side and an inner side.

The separator 36 is in the form of a film and is composed of an elastic material, such as rubber. The separator 36 is connected to an inner wall of the guide sheath 10 so as to separate the bent section 13 into the outer side and the inner side, as viewed in the cross-sectional view of the guide sheath 10 shown in FIG. 31.

With regard to the guide sheath 10 according to this modification, when the guide sheath 10 is to be inserted into the pericardial cavity C, the dilator 23 is inserted along the guide wire 25 through the outer side of the bent section 13 of the guide sheath 10 (i.e., the upper side of the separator 36 in FIG. 31), as shown in FIG. 30. Then, the guide sheath 10 and the dilator 23 are inserted together into the pericardial cavity C.

Subsequently, the dilator 23 is pulled out from the guide sheath 10 so that the distal end of the guide sheath 10 is disposed within the pericardial cavity C and the base end of the guide sheath 10 is disposed outside the body cavity.

Figure 32:
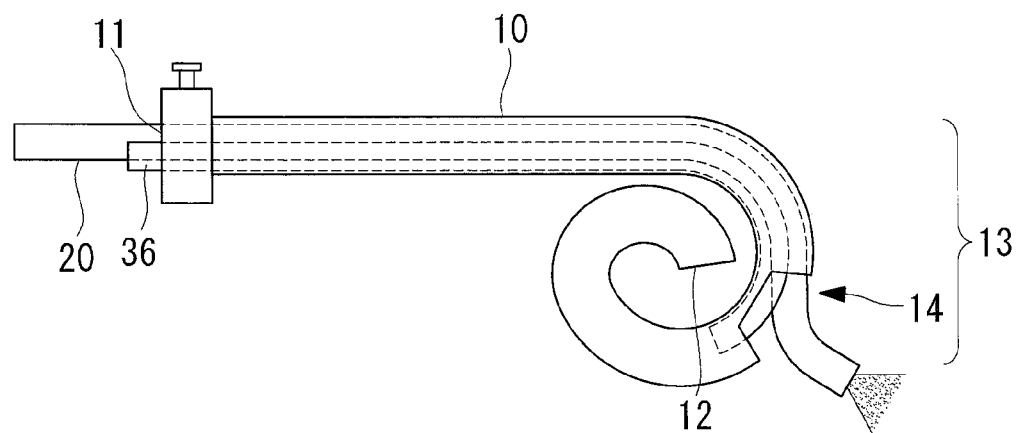
FIG. 32 illustrates a state where the insertion section is inserted into the guide sheath in FIG. 30.

In this case, since the dilator 23 is pulled out from the guide sheath 10, the flexible bent section 13, which was elastically bent to begin with, of the guide sheath 10 deforms into its original shape (i.e., bent shape), as shown in FIG. 32.

In this state, the endoscope insertion section 20 is inserted through the outer side of the bent section 13 of the guide sheath 10 (i.e., the upper side of the separator 36 in FIG. 31) from the base-end opening 11 of the guide sheath 10, as shown in FIG. 32. Consequently, the endoscope insertion section 20 extending through the guide sheath 10 engaged with the inner side of the pericardium B extends out from exit opening 14, whereby the endoscope insertion section 20 is inserted into the pericardial cavity C. Thus, the endoscope can be manipulated within the pericardial cavity C without the guide sheath 10 coming out of the pericardium B, thereby allowing for stable endoscopic observation and treatment within the pericardial cavity C.

Figure 33:
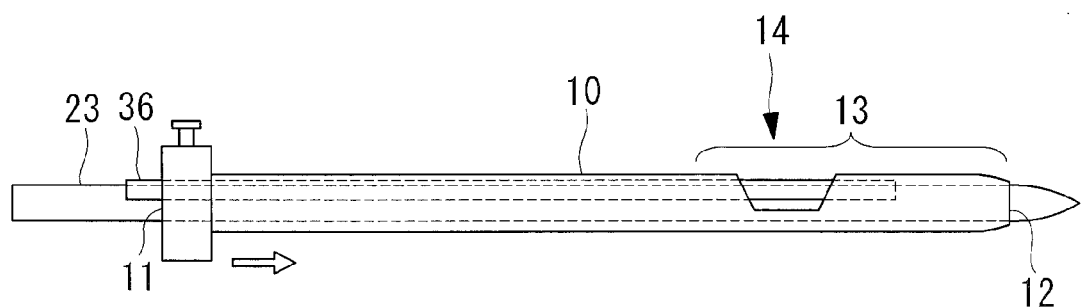
FIG. 33 illustrates a state where the dilator is inserted into the guide sheath in FIG. 30.
Figure 34:
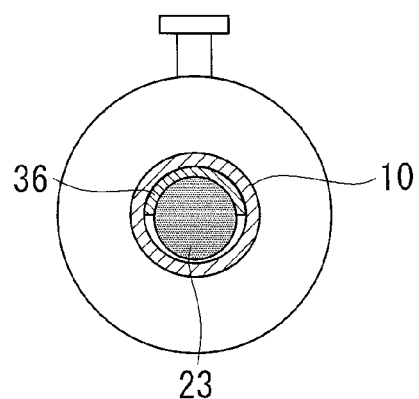
FIG. 34 is a front view of the guide sheath in FIG. 33, as viewed from the base end thereof.

On the other hand, when pulling out the guide sheath 10 from the pericardial cavity C, the dilator 23 is inserted through the inner side of the bent section 13 of the guide sheath 10 (i.e., the lower side of the separator 36 in FIG. 34), as shown in FIGS. 33 and 34. Thus, the dilator 23 extends through the inner side of the bent section 13 of the guide sheath 10 to the distal-end opening 12 of the guide sheath 10, whereby the bent section 13 of the guide sheath 10 can be deformed into a straight shape. Consequently, the guide sheath 10 can be readily pulled out from the pericardial cavity C, whereby the efficiency of the procedure for pulling out the guide sheath 10 from the pericardial cavity C can be improved, and the load on the human body (pericardium B) can be reduced.

By using the film-like separator 36, the cross-sectional area of the separator can be reduced as compared with the case where the tubular separator 35 is used, whereby the inner diameter of the guide sheath 10 can be reduced.

[Sixth Modification]

As a sixth modification of this embodiment, a rotation maintaining mechanism 40 that maintains the guide sheath 10 in a rotated state about its axis may be provided, as shown in FIGS. 35 to 39.

Figure 35:
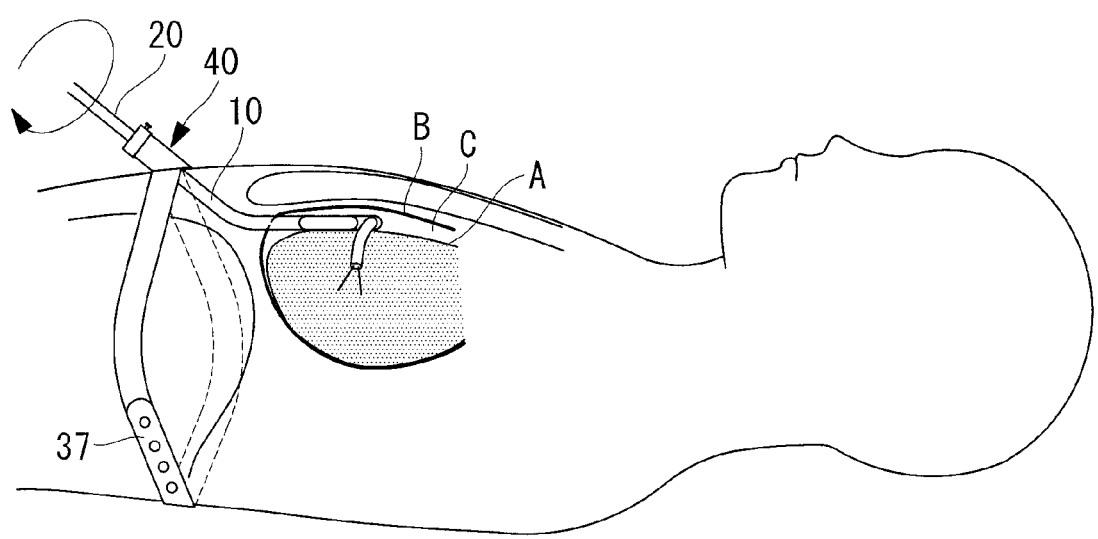
FIG. 35 illustrates a state where the guide sheath in FIG. 1 is provided with a rotation maintaining mechanism, in accordance with a sixth modification.

In the guide sheath 10 according to this modification, the base end of the guide sheath 10 is provided with the rotation maintaining mechanism 40 that maintains the guide sheath 10 in a rotated state about its axis, as shown in FIG. 35. The rotation maintaining mechanism 40 is provided with a strap 37 used for securing the guide sheath 10 to the body surface.

Figure 36:
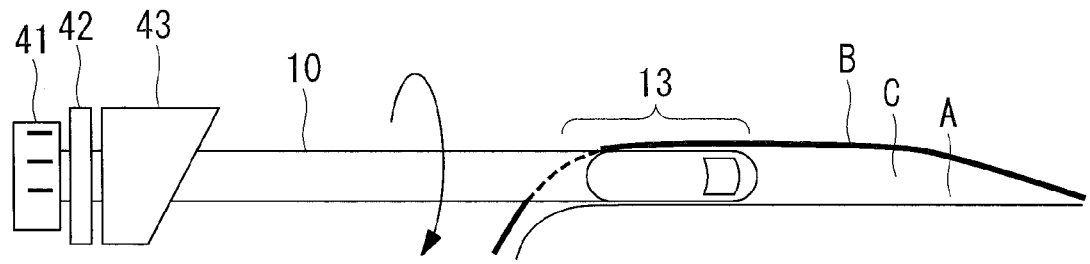
FIG. 36 illustrates the guide sheath in FIG. 35 in its pre-rotated state.
Figure 37:
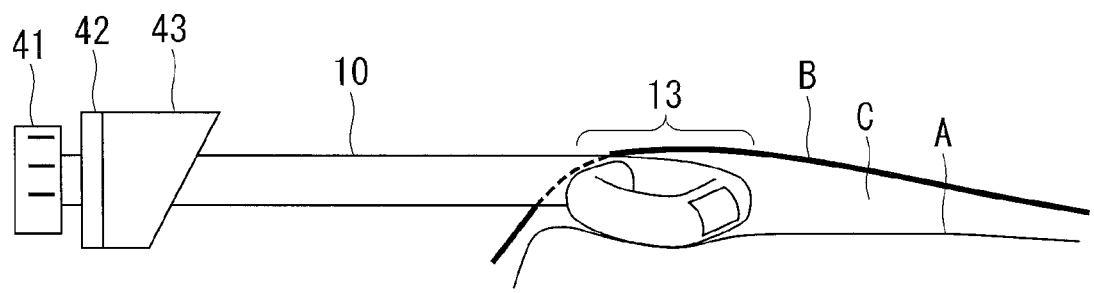
FIG. 37 illustrates the guide sheath in FIG. 35 in its rotated state.

As shown in FIGS. 36 and 37, the rotation maintaining mechanism 40 includes a first component 41 and a second component 42 that are integrally fixed to the guide sheath 10, and a third component 43 provided so as to be rotatable around the axis of the guide sheath 10.

A side surface of the first component 41 is provided with a scale used for checking the rotation angle of the guide sheath 10.

Figure 38:
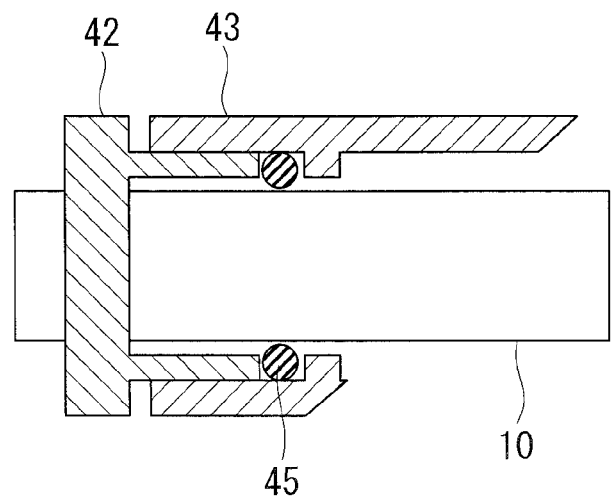
FIG. 38 is an enlarged cross-sectional view of a relevant area of the rotation maintaining mechanism in FIG. 36.

As shown in FIG. 38, the second component 42 is a tubular member integrally fixed to the guide sheath 10 and has a male screw (not shown) around the outer side surface thereof (i.e., a surface in contact with the third component 43).

As shown in FIG. 38, the third component 43 is a tubular member provided so as to be rotatable around the axis of the guide sheath 10 and has a female screw (not shown) around the inner side surface (i.e., a surface in contact with the second component 42) thereof.

Figure 39:
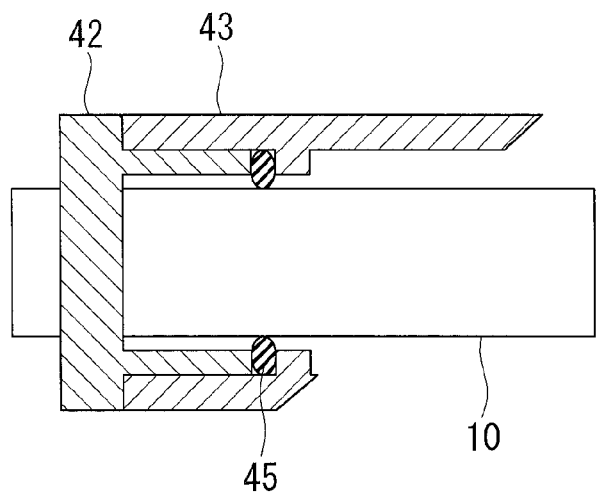
FIG. 39 is an enlarged cross-sectional view of the relevant area of the rotation maintaining mechanism in FIG. 37.

The third component 43 is disposed at the outer side of the second component 42, and an elastic gasket 45 composed of, for example, rubber is provided between the guide sheath 10 and the third component 43 (i.e., between the second component 42 and the third component 43). By rotating the first component 41 (i.e., the guide sheath 10) about the axis, the second component 42 and the third component 43 become engaged with each other. In this case, as shown in FIG. 39, the gasket 45 becomes biased in the axial direction of the guide sheath 10 by the second component 42 so as to deform and expand inward in the radial direction of the guide sheath 10. Thus, the guide sheath 10 becomes biased inward in the radial direction by the gasket 45, whereby the rotation angle of the guide sheath 10 is maintained.

With the guide sheath 10 according to this modification equipped with the rotation maintaining mechanism 40 having the above-described configuration, the guide sheath 10 is rotated about its axis as shown in FIG. 36 so that the pericardium B is pressed upward by the bent section 13, as shown in FIG. 37, whereby a gap can be formed in the pericardial cavity C. In this state, the guide sheath 10 is maintained in position by the rotation maintaining mechanism 40 in the state where the gap is formed in the pericardial cavity C, thereby allowing for improved ease of use when performing observation and treatment in the pericardial cavity C.

[Seventh Modification]

Figure 40:
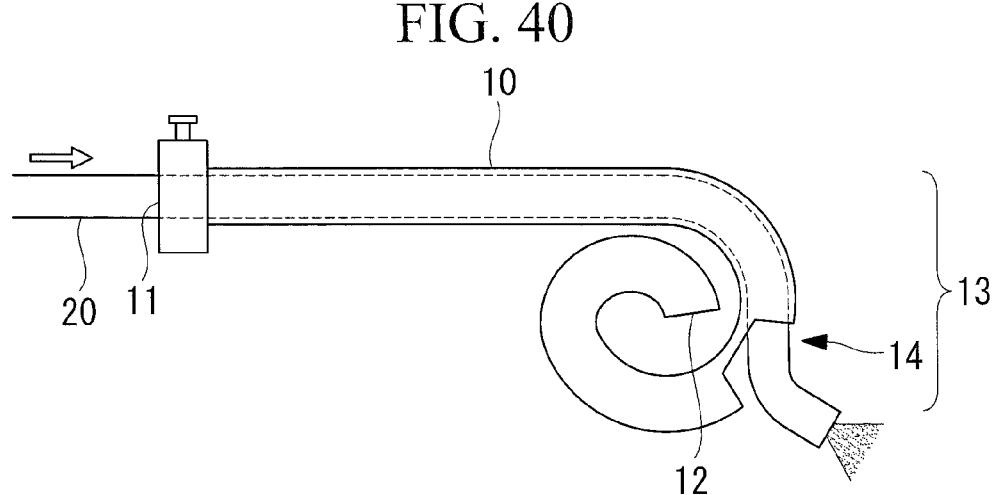
FIG. 40 schematically illustrates the configuration of a guide sheath according to a seventh modification.
Figure 41:
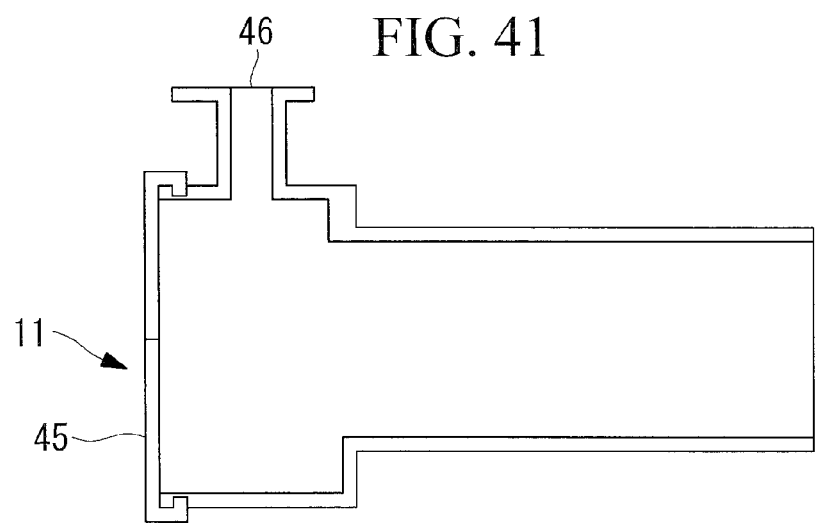
FIG. 41 is an enlarged cross-sectional view of the base end of the guide sheath in FIG. 40.

As a seventh modification of this embodiment, an air-sealing unit, that is, an airtight seal member 45, may be provided at the base-end opening 11 of the guide sheath 10, as shown in FIGS. 40 and 41.

As shown in FIG. 41, the seal member 45 has a slit so that the dilator 23, the endoscope insertion section 20, and the like can be inserted through the base-end opening 11. As an alternative to a slit, a circular hole with a diameter of about 1 mm may be provided. The seal member 45 is composed of an elastic material, such as rubber. When the dilator 23, the endoscope insertion section 20, or the like is inserted through the base-end opening 11, the rubber material expands and contracts so as to seal the gap therebetween.

Accordingly, when the pericardium B is to be expanded by sending air into the pericardial cavity C, the air can be prevented from leaking from the base end of the guide sheath 10, thereby reliably ensuring a site for the operation.

Furthermore, by connecting an air-pressure measuring device via the base-end opening 11 of the guide sheath 10, the internal pressure in the guide sheath 10, that is, the internal pressure in the pericardial cavity, can be measured. Since an excessively high internal pressure in the pericardial cavity can lead to a complication, such as cardiac tamponade, enhanced safety can be achieved by measuring the internal pressure in the pericardial cavity.

Furthermore, as shown in FIG. 41, a port 46 is provided at the upper side of the guide sheath 10. This port 46 may be of a standard Luer lock type. A fluid can be injected into or suctioned from the guide sheath 10 through this port 46. By performing this operation, a saline solution can be fed into the pericardial cavity and treatment can be performed while circulating the saline solution within the pericardial cavity. Furthermore, by feeding gas, such as carbon dioxide, the pericardial cavity can be expanded so that an observation space can be ensured. Needless to say, the fluid can also be suctioned from the same port 46. Moreover, the aforementioned air-pressure measuring device may be connected via this port 46.

[Eighth Modification]

Figure 42:
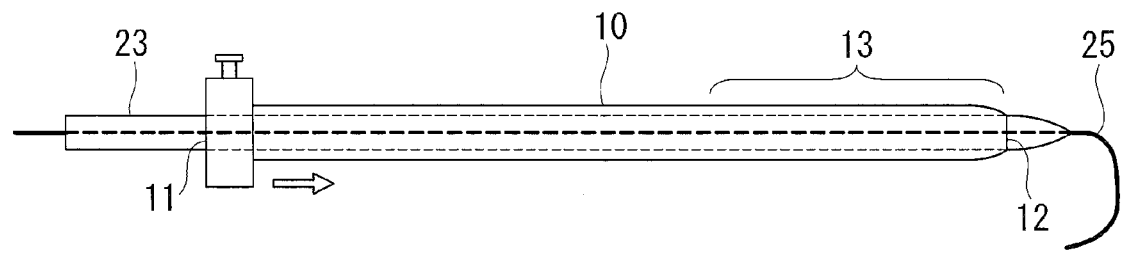
FIG. 42 schematically illustrates the configuration of a guide sheath according to an eighth modification.
Figure 43:
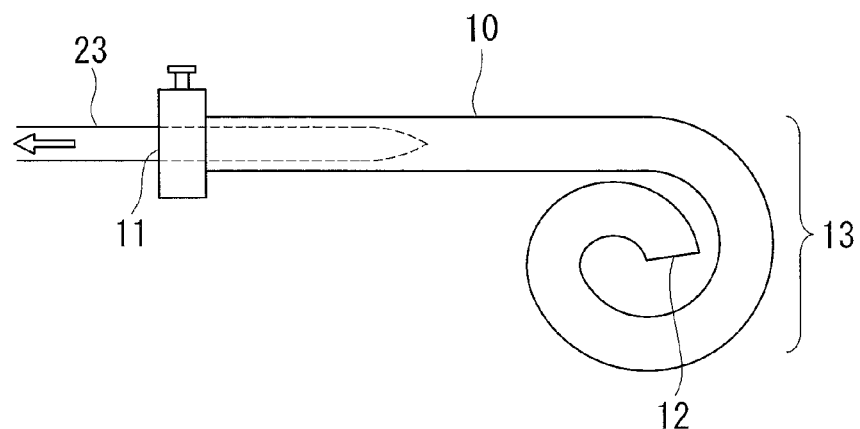
FIG. 43 illustrates a state where the dilator is being pulled out from the guide sheath in FIG. 42.
Figure 44:
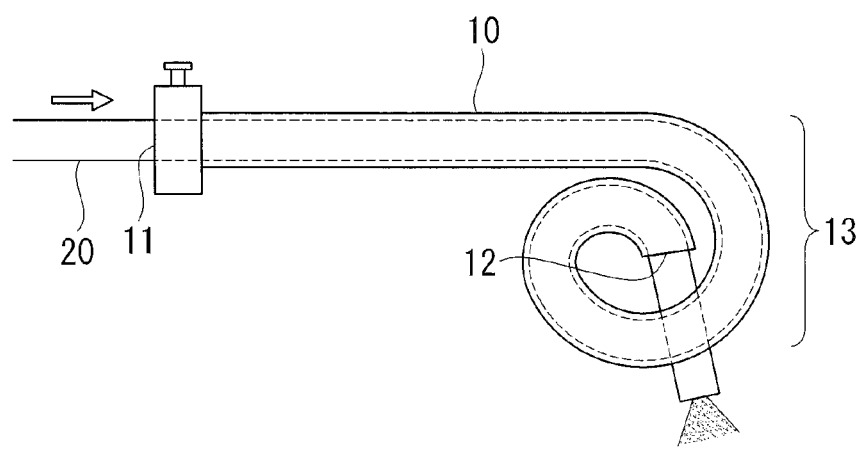
FIG. 44 illustrates a state where the insertion section is inserted into the guide sheath in FIG. 42.

As an eighth modification of this embodiment, instead of providing the bent section 13 of the guide sheath 10 with the exit opening 14, the endoscope insertion section 20 may extend out from the distal-end opening 12, as shown in FIGS. 42 to 44.

With regard to the guide sheath 10 according to this modification, when the guide sheath 10 is to be inserted into the pericardial cavity C, the dilator 23 is inserted into the guide sheath 10 along the guide wire 25, as shown in FIG. 42. Then, the guide sheath 10 and the dilator 23 are inserted together into the pericardial cavity C.

Subsequently, the dilator 23 is pulled out from the guide sheath 10 so that the distal end of the guide sheath 10 is disposed within the pericardial cavity C and the base end of the guide sheath 10 is disposed outside the body cavity.

In this case, since the dilator 23 is pulled out from the guide sheath 10, the bent section 13, which was elastically bent to begin with, of the guide sheath 10 deforms into its original shape (i.e., bent shape), as shown in FIG. 43.

In this state, the endoscope insertion section 20 is inserted through the base-end opening 11 of the guide sheath 10, as shown in FIG. 44. Thus, the endoscope insertion section 20 extending through the guide sheath 10 engaged with the inner side of the pericardium B extends out from the distal-end opening 12, whereby the endoscope insertion section 20 is inserted into the pericardial cavity C. Thus, the endoscope can be manipulated within the pericardial cavity C without the guide sheath 10 coming out of the pericardium B, thereby allowing for stable endoscopic observation and treatment within the pericardial cavity C.

[Ninth Modification]

Figure 47:
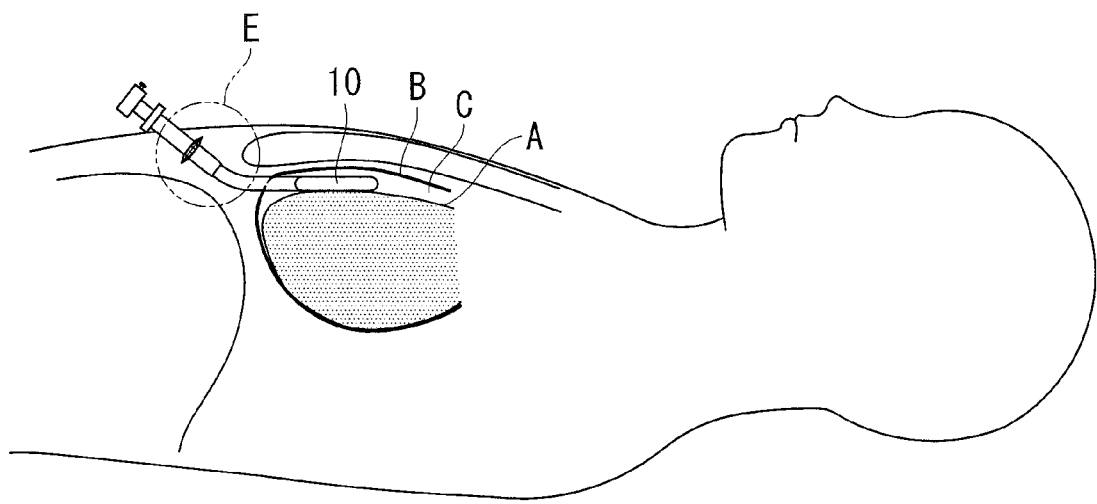
FIG. 47 illustrates a state where the expanding mechanism in FIG. 45 is actuated within the body cavity.

As a ninth modification of this embodiment, the base end of the guide sheath 10 may be provided with an expanding mechanism 50 that expands the guide sheath 10 in the radially outward direction thereof, as shown in FIGS. 45 to 47.

As shown in FIGS. 45 and 46, the expanding mechanism 50 includes a tubular member 51 fixed to the outer side surface of the guide sheath 10, a tubular member 52 provided around the outer surface of the guide sheath 10 in a movable manner in the axial direction, and an expanding section 53 provided between the tubular member 51 and the tubular member 52.

The tubular member 52 has, for example, a ratchet mechanism that becomes locked when moved in the axial direction of the guide sheath 10.

The expanding section 53 has slits provided in the axial direction of the guide sheath 10 and a folding line provided in the circumferential direction of the guide sheath 10. With this configuration, the expanding section 53 is configured to expand in the radially outward direction of the guide sheath 10 when the tubular member 52 is moved toward the distal end of the guide sheath 10 in the axial direction, as shown in FIG. 46.

Accordingly, by expanding the expanding mechanism 50 in the radially outward direction of the guide sheath 10, the expanding mechanism 50 can be engaged with an inner wall of the body cavity (i.e., an area denoted by reference character E in FIG. 47), as shown in FIG. 47. Thus, the guide sheath 10 can be more reliably prevented from coming out of the body cavity.

[Tenth Modification]

Figure 48:
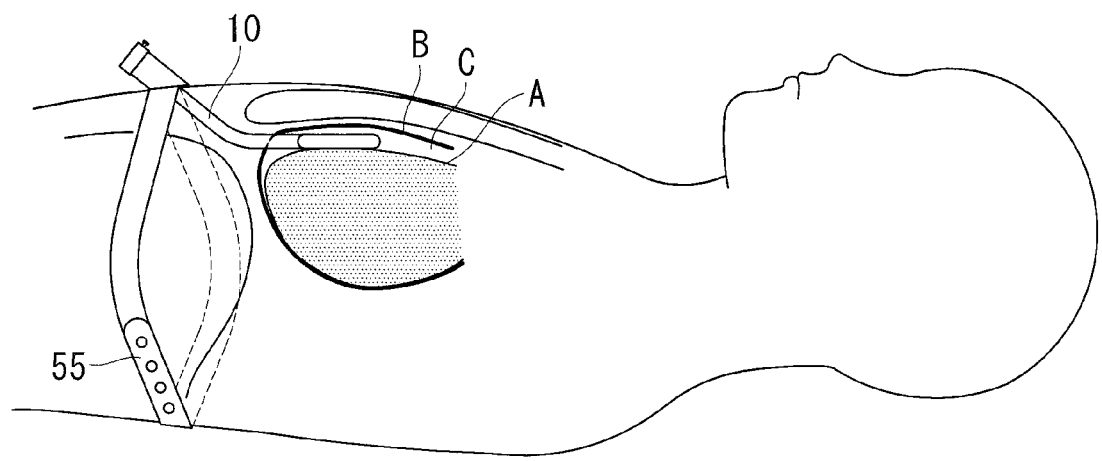
FIG. 48 schematically illustrates the configuration of a guide sheath according to a tenth modification.

As a tenth modification of this embodiment, the base end of the guide sheath 10 may be provided with a strap 55 for securing the guide sheath 10 to the body surface, as shown in FIG. 48.

Accordingly, in addition to the bent section 13 being engaged with the inner side of the pericardium B, the guide sheath 10 can be secured to the body surface by using the strap 55. Thus, the guide sheath 10 can be more reliably prevented from coming out of the body cavity.

Although the above embodiment of the present invention and the modifications thereof have been described in detail above with reference to the drawings, the specific configurations are not limited to the embodiment, and design modifications are encompassed within the scope of the invention so long as they do not depart from the spirit of the invention. For example, the present invention may be applied to embodiments achieved by appropriately combining the above embodiment and the modifications.

The following aspects are derived from the embodiment and the modifications described above.

[Additional Item 1]

A method for setting a guide sheath inside a body cavity, the guide sheath having a bent section, which is elastically bent, and guiding an insertion section of a medical device into the body cavity, the method including:

a step of inserting a distal end of a guide wire into the body cavity;

a step of inserting a base end of the guide wire into the guide sheath and a distal-end hole of a dilator;

a step of inserting the guide sheath and the dilator into the body cavity along the guide wire; and a step of engaging the bent section with the body cavity by pulling out the dilator in a state where the bent section of the guide sheath is inserted into the body cavity.

[Additional Item 2]

A method for pulling out a guide sheath from a body cavity, the guide sheath having a bent section, which is elastically bent, and guiding an insertion section of a medical device into the body cavity, the method including:

a step of inserting the insertion section into the guide sheath set within the body cavity;

a step of straightening the bent section of the guide sheath into a straight shape by using a bending mechanism of the insertion section; and a step of pulling out the guide sheath from the body cavity in a state where the bent section of the guide sheath is maintained in the straight shape.

[Additional Item 3]

A method for pulling out a guide sheath from a body cavity, the guide sheath having a bent section, which is elastically bent, and guiding an insertion section of a medical device into the body cavity, the method including:

a step of inserting a hollow catheter, which is elastically bent, into the guide sheath set within the body cavity;

a step of inserting the catheter to a distal end of the guide sheath;

a step of straightening the guide sheath into a straight shape by inserting a linear core rod into a hollow section of the catheter; and a step of pulling out the guide sheath from the body cavity.

REFERENCE SIGNS LIST

A heart
B pericardium
C pericardial cavity
1 guide sheath system
10 guide sheath
11 base-end opening
12 distal-end opening
13 bent section
14 exit opening
20 insertion section
23 dilator
25 guide wire
27 puncture needle
29 catheter
31 wire
33 tow wire
35, 36 separator
37 strap
40 rotation maintaining mechanism
45 seal member (air-sealing unit)
50 expanding mechanism
55 strap

The invention claimed is:

1. A guide sheath system comprising:
a guide sheath for guiding an insertion section of a medical device, the guide sheath comprising:
a tubular body having a base end and a distal end, the tubular body defining:
a base-end opening at the base end of the tubular body, the base-end opening being configured to receive the insertion section of the medical device; and
a distal-end opening at the distal end of the tubular body,
wherein the tubular body comprises:
a curved section arranged to be closer to the distal end of the tubular body than the base end of the tubular body, the curved section being configured to be elastically deformed, in response to a force on the curved section, from a curved configuration to a straightened configuration, and to elastically return to the curved configuration upon removal of the force on the curved section; and
a proximal section arranged between the curved section and the base end of the tubular body, the proximal section defining an insertion direction along which the insertion section of the medical device is inserted toward the curved section;
wherein the curved section of the tubular body defines an exit opening that is, in the curved configuration, arranged on an outer curvature side of the curved section, and
wherein in the curved configuration, the exit opening defines an exit direction along which the insertion section of the medical device extends past the exit opening, wherein the exit direction intersects the insertion direction.

2. The guide sheath system according to claim 1, wherein, in the curved configuration, the exit direction and the insertion direction form an angle of 0 degree to 45 degrees.

3. The guide sheath system according to claim 1, wherein, in the curved configuration, the exit direction and the insertion direction form an angle of 45 degrees to 135 degrees.

4. The guide sheath system according to claim 1, wherein, in the curved configuration, the exit direction and the insertion direction form an angle of 135 degrees to 215 degrees.

5. The guide sheath system according to claim 1, further comprising:

a tow wire connected to the distal end of the tubular body, extending toward the base end of the tubular body, and arranged on the outer curvature side of the curved section, wherein the tow wire is configured to be pulled toward the base end of the tubular body to exert the force on the curved section to elastically deform the curved section from the curved configuration to the straightened configuration.

6. The guide sheath system according to claim 1, further comprising a strap configured to secure the tubular body to a body surface.

7. The guide sheath system according to claim 1, further comprising:
a rotation maintaining mechanism configured, while the curved section is in the curved configuration and arranged in a pericardial cavity between a heart and a pericardium, to rotate the tubular body about the insertion axis from a first rotation position to a second rotation position and to maintain the tubular body at the second rotation position.

8. The guide sheath system according to claim 1, further comprising:
an air-sealing material arranged to the base-end opening of the tubular body, wherein the air-sealing material is configured to prevent leakage of air from the tubular body through the base-end opening.

9. The guide sheath system according to claim 1, wherein the tubular body is radiopaque.

10. The guide sheath system according to claim 1, further comprising:
a guide wire configured to be inserted into the base-end opening of the tubular body of the guide sheath, through the tubular body of the guide sheath, and out from the distal-end opening of the tubular body of the guide sheath; and
a rod-shaped dilator configured to be guided by the guide wire and to be removably inserted into the base-end opening of the tubular body of the guide sheath, through the tubular body of the guide sheath, and out from the distal-end opening of the tubular body of the guide sheath, wherein the rod-shaped dilator exerts the force on the curved section to elastically deform the curved section from the curved configuration to the straightened configuration as the rod-shaped dilator is inserted through the curved section towards the distal-end opening of the tubular body of the guide sheath.

11. The guide sheath system according to claim 1, further comprising:
a catheter configured to be inserted into the base-end opening of the tubular body of the guide sheath and through the tubular body of the guide sheath, wherein the catheter is configured to be elastically deformed by the curved section of the tubular body in the curved configuration; and
a linear wire configured to be inserted into the catheter to exert the force on the curved section of the tubular body through the catheter to elastically deform the curved section from the curved configuration to the straightened configuration.

12. A guide sheath system comprising:
an insertion section of a medical device; and
a guide sheath for guiding the insertion section of the medical device, the guide sheath comprising:
a tubular body having a base end and a distal end, the tubular body defining:
a base-end opening at the base end of the tubular body, the base-end opening being configured to receive the insertion section of the medical device; and
a distal-end opening at the distal end of the tubular body,
wherein the tubular body comprises:
a curved section arranged to be closer to the distal end of the tubular body than the base end of the tubular body, the curved section being configured to be elastically deformed, in response to a force on the curved section, from a curved configuration to a straightened configuration, and to elastically return to the curved configuration upon removal of the force on the curved section; and
a proximal section arranged between the curved section and the base end of the tubular body, the proximal section defining an insertion direction along which the insertion section of the medical device is inserted toward the curved section; and
wherein the curved section of the tubular body defines an exit opening that is, in the curved configuration, arranged on an outer curvature side of the curved section, and
wherein in the curved configuration, the exit opening defines an exit direction along which the insertion section of the medical device extends past the exit opening, wherein the exit direction intersects the insertion direction,
wherein the insertion section of the medical device is configured to be removably inserted into the base-end opening of the tubular body of the guide sheath, and through the curved section of the tubular body of the guide sheath, and
wherein the insertion section of the medical device comprises a bending mechanism configured to be actuated to bend the insertion section to thereby exert the force on the curved section to elastically deform the curved section from the curved configuration to the straightened configuration.

* * * * *